US010179927B2

(12) United States Patent
Hinks et al.

(10) Patent No.: US 10,179,927 B2
(45) Date of Patent: Jan. 15, 2019

(54) ELECTROCHEMICAL DETECTION OF MICROORGANISMS

(71) Applicants: NANYANG TECHNOLOGICAL UNIVERSITY, Singapore (SG); NATIONAL UNIVERSITY OF SINGAPORE, Singapore (SG)

(72) Inventors: Jamie Hinks, Singapore (SG); Jing Ying Evelina Han, Singapore (SG); Say Chye Joachim Loo, Singapore (SG); Stefan Wuertz, Singapore (SG)

(73) Assignees: Nanyang Technological University, Singapore (SG); National University of Singapore, Singapore (SG)

( * ) Notice: Subject to any disclaimer, the term of this patent is extended or adjusted under 35 U.S.C. 154(b) by 137 days.

(21) Appl. No.: 15/505,847

(22) PCT Filed: Aug. 24, 2015

(86) PCT No.: PCT/SG2015/050274
§ 371 (c)(1),
(2) Date: Feb. 22, 2017

(87) PCT Pub. No.: WO2016/028233
PCT Pub. Date: Feb. 25, 2016

(65) Prior Publication Data
US 2018/0016618 A1  Jan. 18, 2018

Related U.S. Application Data

(60) Provisional application No. 62/040,792, filed on Aug. 22, 2014.

(51) Int. Cl.
| | |
|---|---|
| *C12Q 1/06* | (2006.01) |
| *G01N 25/08* | (2006.01) |
| *C07H 15/04* | (2006.01) |
| *C07D 279/10* | (2006.01) |
| *C07D 213/00* | (2006.01) |
| *C07C 50/04* | (2006.01) |
| *C12Q 1/10* | (2006.01) |
| *C07H 17/00* | (2006.01) |
| *C12Q 1/04* | (2006.01) |
| *G01N 27/49* | (2006.01) |
| *C07H 15/24* | (2006.01) |
| *G01N 27/327* | (2006.01) |
| *G01N 27/48* | (2006.01) |

(52) U.S. Cl.
CPC ............. *C12Q 1/10* (2013.01); *C07H 15/24* (2013.01); *C07H 17/00* (2013.01); *C12Q 1/04* (2013.01); *C12Q 1/06* (2013.01); *G01N 27/3277* (2013.01); *G01N 27/48* (2013.01); *G01N 27/49* (2013.01); *G01N 2333/924* (2013.01)

(58) Field of Classification Search
None
See application file for complete search history.

(56) References Cited

U.S. PATENT DOCUMENTS

| | | | |
|---|---|---|---|
| 5,336,600 A | 8/1994 | Monget | |
| 5,427,912 A | * 6/1995 | Brown | ................. G01N 33/581 204/403.14 |
| 6,534,637 B2 | 3/2003 | Shen et al. | |
| 7,029,886 B1 | 4/2006 | Armstrong et al. | |
| 2006/0199241 A1 | 9/2006 | Yim et al. | |
| 2007/0003997 A1 | 1/2007 | Kemmochi et al. | |

(Continued)

FOREIGN PATENT DOCUMENTS

| | | |
|---|---|---|
| EP | 2 532 753 A1 | 12/2012 |
| RU | 2 372 919 C2 | 6/2007 |

(Continued)

OTHER PUBLICATIONS

Perez et al. Analytica Chimica Acta 427 (2001) 149-154 (Year: 2001).*
Antonczak et al., "A Critical Examination of *Escherichia coli* Esterase Activity," *The Journal of Biological Chemistry* 284(42):28795-28800, 2009. (7 pages).
Bej et al., "Detection of *Escherichia coli* and *Shigella* spp. in Water by Using the Polymerase Chain Reaction and Gene Probes for *uid*," *Applied and Environmental Microbiology* 57(4): 1013-1017, 1991. (6 pages).
Besant et al., "Rapid electrochemical phenotypic profiling of antibiotic-resistant bacteria," *Lab Chip* 15(13):2799-2807, 2015.

(Continued)

*Primary Examiner* — Jeffrey S Lundgren
*Assistant Examiner* — Michael J Schmitt
(74) *Attorney, Agent, or Firm* — Seed IP Law Group LLP

(57) ABSTRACT

The present invention provides a method for determining the presence of a microorganism in a sample using an electrochemically active reporter, wherein the method comprises (a) contacting the sample with an electrochemically active reporter, wherein the electrochemically active reporter is a conjugate comprising a sugar moiety and a redox active reporter moiety that are covalently linked such that the covalent bond can be enzymatically cleaved in the presence of the microorganism by an enzyme expressed by the microorganism, wherein the redox active reporter moiety is selected from the group consisting of resorufin and compounds of formula (I) as defined herein, under conditions that allow enzymatic cleavage of the covalent bond between the sugar moiety and the redox active reporter moiety and reduction of the redox active report moiety in the presence of the microorganism; (b) electrochemically determining the released redox active reporter moiety; and (c) determining the presence of the microorganism and, optionally, number of the microorganisms in the sample based on the determined released redox active reporter moiety. Also encompassed are the electrochemically active reporters used in the described methods and their use for determination of the presence of microorganisms in a sample.

20 Claims, 8 Drawing Sheets

(56) References Cited

U.S. PATENT DOCUMENTS

2011/0171667 A1   7/2011   Cellier et al.
2014/0212905 A1   7/2014   Spitz et al.

FOREIGN PATENT DOCUMENTS

SU          1088346 A    12/1986
WO      2008/009046 A1    1/2008

OTHER PUBLICATIONS

Cabral, "Water Microbiology. Bacterial Pathogens and Water," *International Journal of Environmental Research and Public Health* 7(10):3657-3703, 2010.

Choi et al., "Dynamic Behaviors of Redox Mediators within the Hydrophobic Layers as an Important Factor for Effective Microbial Fuel Cell Operation," *Bulletin of the Korean Chemical Society* 24(4):437-440, 2003.

Douterelo et al., "Methodological approaches for studying the microbial ecology of drinking water distribution systems," *Water Research* 65:134-156, 2014.

Edberg et al., "*Escherichia coli*: the best biological drinking water indicator for public health protection," *Journal of Applied Microbiology* 88(S1):106S-116S, 2000.

Edberg et al., "National Field Evaluation of a Defined Substrate Method for the Simultaneous Enumeration of Total Coliforms and *Escherichia coli* from Drinking Water: Comparison with the Standard Multiple Tube Fermentation Method," *Applied and Environmental Microbiology* 54(6):1595-1601, 1988.

Fiksdal et al., "Monitoring of Fecal Pollution in Coastal Waters by Use of Rapid Enzymatic Techniques," *Applied and Environmental Microbiology* 60(5):1581-1584, 1994.

Frahm et al., "Application of the fluorogenic probe technique (TaqMan PCR) to the detection of *Enterococcus* spp. and *Escherichia coli* in water samples," *Journal of Microbiological Methods* 52(1):123-131, 2003.

Geissler et al., "Quantitative determination of total coliforms and *Escherichia coli* in marine waters with chromogenic and fluorogenic media," *Journal of Applied Microbiology* 88(2):280-285, 2000.

Hata et al., "Molecular Epidemiology of Cases of *Mycoplasma californicum* Infection in Japan," *Applied and Environmental Microbiology* 80(24):7717-7724, 2014.

International Search Report and Written Opinion, dated Oct. 29, 2015, for International Application No. PCT/SG2015/050274, 11 pages.

James et al., "Environmental Technology Verification Report: Pathogen Detection Systems, Inc. Automated Microbiology Platform," ETV Advanced Monitoring Systems Center, Sep. 2010, 39 pages.

Kapoor et al., "Distribution of Human-Specific *Bacteroidales* and Fecal Indicator Bacteria in an Urban Watershed Impacted by Sewage Pollution, Determined Using RNA- and DNA-Based Quantitative PCR Assays," *Applied and Environmental Microbiology* 81(1):91-99, 2015.

Lan et al., "*Escherichia coli* in disguise: molecular origins of Shigella," *Microbes and Infection* 4(11):1125-1132, 2002.

Lazcka et al., "Pathogen detection: A perspective of traditional methods and biosensors," *Biosensors and Bioelectronics* 22(7):1205-1217, 2007.

Logan, "Exoelectrogenic bacteria that power microbial fuel cells," *Nature Reviews: Microbiology* 7(5):375-381, 2009.

Manafi et al., "Fluorogenic and Chromogenic Substrates Used in Bacterial Diagnostics," *Microbiological Reviews* 55(3):335-348, 1991.

Manafi, "New developments in chromogenic and fluorogenic culture media," *International Journal of Food Microbiology* 60(2-3):205-218, 2000.

Martins et al., "Distribution of *uidA* Gene Sequences in *Escherichia coli* Isolates in Water Sources and Comparison with the Expression of $\beta$-Glucuronidase Activity in 4-Methylumbelliferyl-$\beta$-D-Glucuronide Media," *Applied and Environmental Microbiology* 59(7):2271-2276, 1993.

Nelis et al., "Enzymatic Detection of Coliforms and *Escherichia coli* Within 4 Hours," *Water, Air, and Soil Pollution* 123(1-4):43-52, 2000.

Nshimyimana et al., "Distribution and abundance of human-specific *Bacteroides* and relation to traditional indicators in an urban tropical catchment," *Journal of Applied Microbiology* 116(5):1369-1383, 2014.

Park et al., "Electricity Generation in Microbial Fuel Cells Using Neutral Red as an Electronophore," *Applied and Environmental Microbiology* 66(4):1292-1297, 2000.

Pérez et al., "Rapid detection of *Escherichia coli* in water by a culture-based amperometric method," *Analytica Chimica Acta* 427(2):149-154, 2001.

Pham et al., "A novel electrochemically active and Fe(III)-reducing bacterium phylogenetically related to *Aeromonas hydrophila*, isolated from a microbial fuel cell," *FEMS Microbiology Letters* 223(1):129-134, 2003.

Presswood et al., "Modification of M-FC Medium by Eliminating Rosolic Acid," *Applied and Environmental Microbiology* 36(1):90-94, 1978.

Rau et al., "Effects of Different Quinoid Redox Mediators on the Anaerobic Reduction of Azo Dyes by Bacteria," *Environmental Science & Technology* 36(7):1497-1504, 2002.

Roller et al., "Electron-transfer Coupling in Microbial Fuel Cells: 1. Comparison of Redox-mediator Reduction Rates and Respiratory Rates of Bacteria," *Journal of Chemical Technology and Biotechnology* 34B(1):3-12, 1984.

Rompré et al., "Detection and enumeration of coliforms in drinking water: current methods and emerging approaches," *Journal of Microbiological Methods* 49(1):31-54, 2002.

Song et al., "Metabolic analysis of rhubarb extract by rat intestinal bacteria using liquid chromatography-tandem mass spectrometry," *Biomedical Chromatography* 25(3):417-426, 2011.

Stupp et al., "Chemical Detoxification of Small Molecules by *Caenorhabditis elegans*," *ACS Chemical Biology* 8(2):309-313, 2013.

Sund et al., "Effect of electron mediators on current generation and fermentation in a microbial fuel cell," *Applied Microbiology and Biotechnology* 76(3):561-568, 2007.

Waltman II et al., "Enzymatic Characterization of *Aeromonas hydrophila* Complex by the API ZYM System," *Journal of Clinical Microbiology* 16(4):692-696, 1982.

Wang et al., "Improving charge collection in *Escherichia coli*-carbon electrode devices with conjugated oligoelectrolytes," *Physical Chemistry Chemical Physics* 15(16):5867-5872, 2013.

Zhou et al., "Bioactive Anthraquinone Derivatives from the Mangrove-Derived Fungus *Stemphylium* sp. 33231," *Journal of Natural Products* 77(9):2021-2028, 2014.

Bakunina et al., "Effect of 5-hydroxy- and 5,8-dihydroxy-1,4-naphthoquinones on the hydrolytic activity of $\alpha$-galactosidase," *Chemistry of Natural Compounds* 45(1):69-73, 2009.

Extended European Search Report, dated Mar. 21, 2018, for European Application No. 15834322.8-1111 / 3183362, 10 pages.

Hinks et al., "Naphthoquinone glycosides for bioelectroanalytical enumeration of the faecal indicator *Escherichia coli*," *Microbial Biotechnology* 9:746-757, 2016.

Kaya et al., "On-chip electrochemical measurement of $\beta$-galactosidase expression using a microbial chip," *Chem. Commun.* 2:248-249, 2004.

Khazalpour et al., "Electrochemical study of Alamar Blue (resazurin) in aqueous solutions and room-temperature ionic liquid 1-butyl-3-methylimidazolium tetrafluoroborate at a glassy carbon electrode," *RSC Adv.* 4:8431-8438, 2014.

Kim et al., "Fast detection and quantification of *Escherichia coli* using the base principle of the microbial fuel cell," *Journal of Environmental Management* 130:267-275, 2013.

Magro et al., "Synthesis and Application of Resorufin $\beta$-D-Glucuronide, a Low-Cost Chromogenic Substrate for Detecting *Escherichia coli* in Drinking Water," *Environ. Sci. Technol.* 48:9624-9631, 2014.

(56) References Cited

OTHER PUBLICATIONS

Mittelmann et al., "Amperometric Quantification of Total Coliforms and Specific Detection of *Escherichia coli*," *Anal. Chem.* 74(4);903-907, 2002.

Serra et al., "In-a-Day Electrochemical Detection of Coliforms in Drinking Water Using a Tyrosinase Composite Biosensor," *Anal. Chem.* 77(24):8115-8121, 2005.

Tao et al., "Development of spiropyran-based electrochemical sensor via simultaneous photochemical and target-activatable electron transfer," *Biosensors and Bioelectronics* 62:151-157, 2014.

Togo et al., "Novel detection of *Escherichia coli* β-D-glucuronidase activity using a microbially-modified glassy carbon electrode and its potential for faecal pollution monitoring," *Biotechnol Lett* 29:531-537, 2007.

\* cited by examiner

ELECTROCHEMICAL DETECTION OF MICROORGANISMS

CROSS-REFERENCE TO RELATED APPLICATION

This application makes reference to and claims the benefit of priority of a U.S. Provisional Application for "Electrochemical Detection of *E. coli*" filed on Aug. 22, 2014, and duly assigned application No. 62/040,792. The content of said application filed on Aug. 22, 2014 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention lies in the field of microorganism detection, and particularly relates to the bioelectrochemical detection of a microorganism in a sample, preferably in an environmental or biological sample, using an electrochemically active reporter recognizable and cleavable by an enzyme expressed by the microorganism to be determined.

BACKGROUND OF THE INVENTION

Detection of microorganisms is routinely performed in testing environmental and biological samples. For example, as a public health protection measure, many countries mandate that utility providers monitor recreational and potable water for microorganisms that are indicators of faecal contamination. Faecal contamination of water bodies in urban environments arises from inadequate waste management in, for example, developing countries, or from failure of water management systems, such as leakage from compromised or overburdened sewerage networks. Faecal contamination can also occur in drinking water distribution systems from sewage or drainage ingress when water mains experience transient depressurization, such as during maintenance or pump failure. There is a link between exposure to human waste and the transmission of infectious diseases such as cholera, typhoid fever, shigellosis and acute gastroenteritis. Considerable effort is expended in detecting, quantifying and tracking instances of faecal contamination of water bodies to ensure drinking water meets sanitary guidelines and that recreational waters remain safe for primary and secondary contact activities such as swimming and boating respectively. The monitoring of microbial water quality is routinely undertaken by or on behalf of, local authorities or utilities who will use the information to control public access to recreational facilities and water resources.

Usually, faecal indictor bacteria (FIB) are monitored as a proxy for faecal contamination of water, traditionally relying on the enumeration of faecal coliforms (FC), usually understood to mean *E. coli,* and total coliforms (TC), to assess microbial water quality. FIB, not necessarily disease causing themselves, must fulfil a number of criteria, including low tendency to proliferate in the hydrosphere, to be nonpathogenic, to persist longer than pathogens in the hydrosphere, and to have known provenance of either human or animal origin (Nshimyimana et al., J. Appl. Microbiol. 2014; 116 (5):1369-83; Cabral, Int. J. Environ. Res. Public Health. 2010; 7(10):3657-703). Alternative indicators, such as *Enterococcus faecalis, Clostridium perfringens* and *Bacillus* spp. have also been used as FIB in an attempt to more definitively identify human faecal contamination of water (Douterelo et al., Water Res. 2014; 65:134-156; U.S. patent application Ser. No. 11/428,046). There are a number of drawbacks to using FIB as a proxy for detection of faecal contamination many of which stem from the indirect nature of the procedure, the length of time required for growth, and the assumptions underlying FIB selection. Recently, molecular advances have allowed the monitoring of emerging faecal indicators which were previously impossible with culture based techniques, such as real time PCR detection of the uidA gene or the human specific bacteroides HF183 marker (Nshimyimana et al., J. Appl. Microbiol. 2014; 116(5):1369-83).

While it is true that specificity and detection time can be improved by molecular techniques, their direct correlation to pollution quantity remains unsatisfactorily resolved and hence does their application to improve risk based decision making. For example, PCR consistently underestimates the proportion of bifidobacterium when compared with culture based methods, which results in positive detection of organisms that are not detected by regulatory approved culture based techniques (Cabral, Int. J. Environ. Res. Public Health. 2010; 7(10):3657-703).

Modern enzymatic assays and many molecular and traditional culture techniques for the enumeration of *E. coli* or FC exploit the uidA gene which encodes for the β-glucuronidase enzyme and which almost 98% of *E. coli* possess (Martins et al., Appl. Environ. Microbiol. 1993; 59(7):2271-6; Manafi et al., Microbiol. Rev. 1991; 55(3):335-48). Similarly, the lacZ gene which encodes for β-galactosidase is indicative of TC, such as *Klebsiella* spp., *Citrobacter* spp., as well as *E. coli* (Cabral, Int. J. Environ. Res. Public Health. 2010; 7(10):3657-703; Manafi et al., Microbiol. Rev. 1991; 55(3):335-48; Bej et al., Appl. Environ. Microbiol. 1991; 57(4):1013-7). The current technology for commercial *E. coli* detection usually involves a uidA or lacZ specific monosaccharide conjugated to a chromogenic or fluorogenic compound (aglycon). When cleaved by the action of the corresponding enzyme found in the uidA or lacZ gene region, the optically active aglycon is released into the medium and is subsequently detected either spectroscopically, by visual assessment, by fluorimetery or inspection under a UV lamp (Manafi et al., Microbiol. Rev. 1991; 55(3):335-48; Nelis and Van Poucke, Environmental Challenges. Springer) and thus the organism of interest is presumed present.

Enzymatic, and culture based approaches may be biased, labour intensive, expensive and prone to interference from the natural properties of environmental samples, such as humic acid content, turbidity and non-target organisms (Hata et al., Appl. Environ. Microbiol. 2014; Kapoor et al., Appl. Environ. Microbiol. 2015; 81:91-99). However, the current regulatory favoured technique for evaluation of microbial water quality still remains the culture based or enzymatic enumeration of TC or FC. These approaches are predominantly laboratory-based, labour intensive and suffer from poor detection times. These shortcomings have not been satisfactorily resolved, which leaves significant opportunity for innovation to achieve faster detection at low cost (Rompréet al., J. Microbiol. Methods. 2002; 49:31-54).

Regardless of the approach, fast and automated detection of FIB that do not require specialist operators is desirable because of the cost savings that could be achieved through reduced labour costs and higher throughput. Even as the range of indicator proxies expands and the potential transduction framework and detection technology increases (Lazcka et al., Biosensors and Bioelectronics 2007; 22:1205-1217), there still remains regulatory resistance to emerging FIB detection techniques. Consequently, no regulatory guidelines exist in the EU or the US that prescribe standard protocols for the application of molecular approaches to FIB monitoring and all approved approaches are for laboratory based chromogenic, fluorogenic or traditional culture based methods (Douterelo et al., Water Res. 2014; 65:134-156).

Electrochemical detection of *E. coli* using glycoconjugates has been reported previously with reasonable detection times (Perez et al., Anal. Chim. Acta. 2001; 427:149-154.). Perez et al. reported the detection of *E. coli* at concentrations of 1 CFU mL$^{-1}$ (laboratory sample) and 4.5 CFU mL$^{-1}$ (marine sample) in 10 h and in 7.3 h respectively. However, in addition to a filtration step, the method described by Perez et al. utilized a combination of flow injection analysis (FIA), and a potentiostatic technique to achieve sensitive electrochemical detection of a 4-aminophenyl (4-AP) aglycon that had been cleaved from 4-aminophenyl-β-d-galactopyranoside (4-APgal) glycoconjugate by *E. coli*. The complexity and low throughput of this method make it incompatible with automated or remote applications as it requires skilled operation.

Low cost bioelectroanalytical methods would be amenable to automation and portable applications. However, for self-powering systems to work, the aglycon component of the detection compounds needs to be reversibly oxidized by microorganisms to achieve microbially mediated electron transfer to the electrode as *E. coli* is not strongly electrogenic in character (Wang et al., Phys. Chem. Chem. Phys. 2013; 15:5867-5872; Choi et al., BULLETIN-KOREAN CHEMICAL SOCIETY 2003; 24:437-440; Roller et al., J. Chem. Technol. Biotechnol. 1984; 34:3-12). Theoretically, electrochemical detection compounds could achieve more sensitive and faster *E. coli* detection than chromogenic equivalents because upon being cleaved, the aglycon component of the glycoconjugate detection compound is able to contribute to signal intensity many times as it may mediate numerous redox interactions between the microorganism and the electrode. Conversely, the contribution to the overall signal of a chromogenic aglycon is merely addictive. Compounds that are commonly used in coliform detection framework, such as 4-APgal and 4-nitrophenol-β-d-glucuronidase (4-NPglu) have been designed for colorimetric and fluorimetric assays. Although they have some electrochemical activity, their redox chemistry is not fully reversible by *E. coli* under physiological conditions or the redox reactions suffer from slow kinetics. Hence their utility in bioelectroanalytical detection is restricted to techniques described by Perez et al. that do not rely on or exploit the microbially mediated electron transfer that is achievable in bioelectranalytical systems.

Therefore, there is still need in the art for alternative methods that overcome the drawbacks of existing techniques.

SUMMARY OF THE INVENTION

The inventors of the present application have found that said need can be met by electrochemical detection methods that employ suitable redox active reporter molecules. Based on the studies on a range of commercially available compounds and redox active molecules, the inventors have identified electrochemically reversible compounds for determining the presence of a microorganism in a sample using an electrochemical system or self-powering bioelectrochemical system. Bioelectroanalytical techniques are emerging as ways to enumerate and scrutinize microbial systems. But there is still need in the art for technologies specifically designed for bioelectroanalytical detection of FIB. In this context, some detection compounds widely used for colorimetric detection of microorganisms, e.g. 4-APgal, 4-NPglu and 8-hydroxyquinoline glucuronide for *Escherichia coli* and 4-methylumbeliferone-glucoside for *Enterococcus faecalis*, have been tested for their potential use in electrochemical detection of microorganisms. However, the inventors have found that these compounds are not well suited for bioelectrochemical detection because of either poor kinetics, a mismatch in potential between the electrode, the redox mediator and the microorganism, or because the redox reaction is not reversible under growth conditions. The latter, in particular, makes them unsuitable in self-powering systems.

In one aspect, the present invention relates to a method for determining the presence of a microorganism in a sample using an electrochemically active reporter, wherein the method comprises (a) contacting the sample with an electrochemically active reporter, wherein the electrochemically active reporter is a conjugate comprising a sugar moiety and a redox active reporter moiety that are covalently linked such that the covalent bond can be enzymatically cleaved in the presence of the microorganism by an enzyme expressed by the microorganism, wherein the redox active reporter moiety is selected from the group consisting of resorufin (7-Hydroxy-3H-phenoxazin-3-one) and compounds of formula (I)

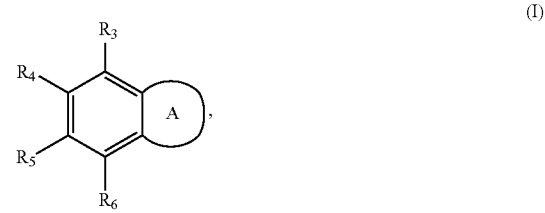

wherein A is an aryl or heteroaryl ring of formula (II) or (III):

each of $R_1$-$R_6$ is independently selected from the group consisting of H, $NR_7R_8$, $C_{1-10}$ Alkyl, and $OR_7$, or $R_1$ and $R_2$ combine together with the carbon atoms to which they are attached to form a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$;

X is N or S$^+$;

$R_7$ and $R_8$ are independently selected from the group consisting of H, C(O)—$R_9$, and $C_{1-10}$ Alkyl;

$R_9$ is $C_{1-10}$ Alkyl, under conditions that allow enzymatic cleavage of the covalent bond between the sugar moiety and the redox active reporter moiety and reduction of the redox active report moiety in the presence of the microorganism;

(b) electrochemically determining the released redox active reporter moiety; and (c) determining the presence of the microorganism and, optionally, number of the microorganisms in the sample based on the determined released redox active reporter moiety.

In various embodiments of the method, the method is carried out by a 3-electrode electrochemical system or a 2-electrode self-powering bioelectrochemical system comprising a working electrode and an electrolyte, the method preferably comprising (a) adding the sample and an effective amount of the electrochemically active reporter to the electrolyte;

(b) measuring the electrical current or voltage resulting from the released redox active reporter moiety by chronoamperometry, potentiometry or voltammetry or other standard electrochemical technique using the electrochemical system or by determining the potential difference between the anode and cathode in the self-powering bioelectrochemical system; and (c) determining the number of the microorganisms in the sample based on the electrical signal measured by comparing it to a predetermined standard curve.

In another aspect, the invention is directed to an electrochemically active reporter for determining the presence of a microorganism in a sample, wherein the electrochemically active reporter is a conjugate comprising a sugar moiety and a redox active reporter moiety that are covalently linked such that the covalent bond can be enzymatically cleaved in the presence of the microorganism by an enzyme expressed by the microorganism, wherein the redox active reporter moiety is selected from the group consisting of resorufin and compounds of formula (I)

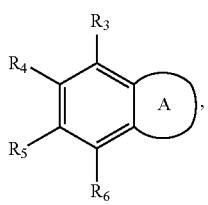

(I)

wherein A is an aryl or heteroaryl ring of formula (II) or (III):

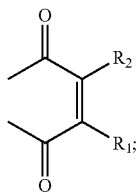

(II)

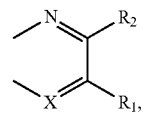

(III)

each of $R_1$-$R_6$ is independently selected from the group consisting of H, $NR_7R_8$, $C_{1-10}$ alkyl, and $OR_7$, or $R_1$ and $R_2$ combine to form together with the carbon atoms to which they are attached a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$;

X is N or $S^+$;

$R_7$ and $R_8$ are independently selected from the group consisting of H, C(O)—$R_9$, and $C_{1-10}$ Alkyl; $R_9$ is $C_{1-10}$ Alkyl.

In still another aspect, the invention encompasses use of an electrochemically active reporter comprising a sugar moiety and a redox active reporter moiety that are covalently linked such that the covalent bond can be enzymatically cleaved in the presence of a microorganism by an enzyme expressed by the microorganism for determination of the presence of said microorganism in a sample, wherein the redox active reporter moiety is selected from the group consisting of resorufin and compounds of formula (I)

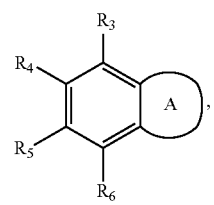

(I)

wherein A is an aryl or heteroaryl ring of formula (II) or (III):

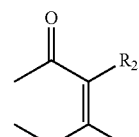

(II)

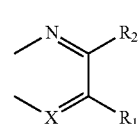

(III)

each of $R_1$-$R_6$ is independently selected from the group consisting of H, $NR_7R_8$, $C_{1-10}$ alkyl, and $OR_7$, or $R_1$ and $R_2$ combine to form together with the carbon atoms to which they are attached a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$;

X is N or $S^+$;

$R_7$ and $R_8$ are independently selected from the group consisting of H, C(O)—$R_9$, and $C_{1-10}$ Alkyl;

$R_9$ is $C_{1-10}$ Alkyl.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
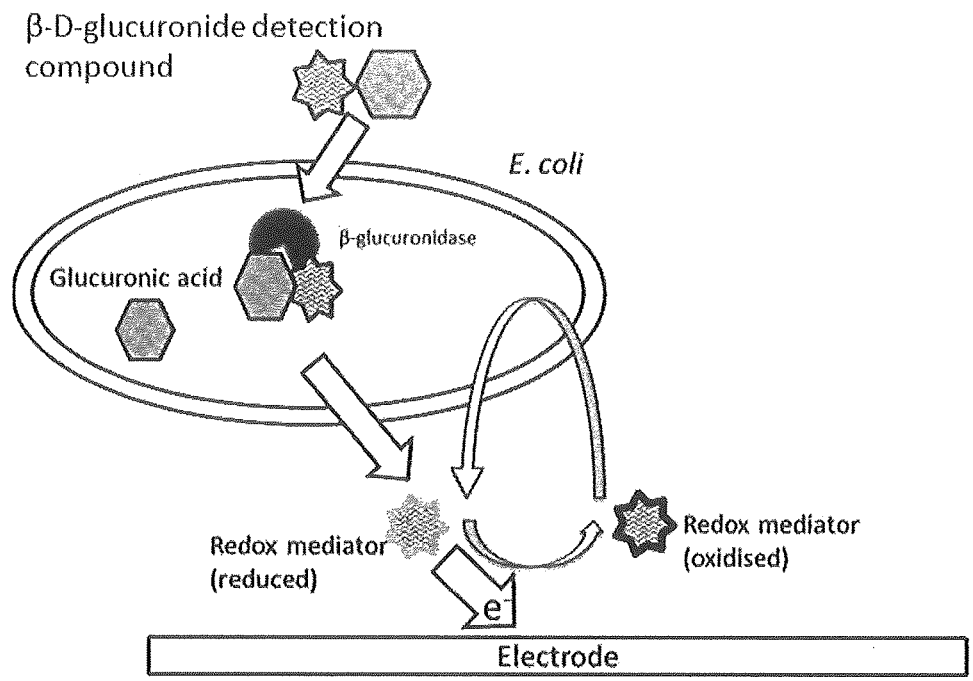
FIG. 1 shows a schematic of the method of the present invention. Note that the redox active reporter moiety of the electrochemically active reporter can be reactivated and recycled by E. coli, amplifying the detection signal. This is contrary to colourimetric compounds where the contribution to the detection signal is additive.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. In case of conflict, the present document, including definitions, will control.

The object of the present invention is to provide a technique for determining the presence of a microorganism in a sample, taking advantage of an enzyme expressed in the target microorganism and an electrochemically active reporter that is recognizable and cleavable by the enzyme. According to the present invention, the electrochemically active reporter comprises a redox active reporter moiety that will be released from said reporter by action of the enzyme in the presence of the microorganism to be determined, said redox active reporter moiety being recycled by the microorganism for the generation of a signal detectable by an electrochemical means. By electrochemically determining the released redox active reporter moiety, the amount of which is approximately proportional to the activity of the microorganism in the sample, the presence and optionally also the amount of the microorganism can be determined.

To this end, in one aspect the present invention relates to a method for determining the presence of a microorganism in a sample using an electrochemically active reporter, wherein the method comprises (a) contacting the sample with an electrochemically active reporter, wherein the electrochemically active reporter is a conjugate comprising a sugar moiety and a redox active reporter moiety that are covalently linked such that the covalent bond can be enzymatically cleaved in the presence of the microorganism by an enzyme expressed by the microorganism, wherein the redox active reporter moiety is selected from the group consisting of resorufin (7-Hydroxy-3H-phenoxazin-3-one) and compounds of formula (I)

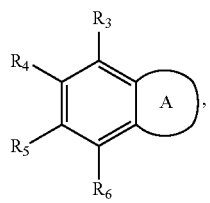

(I)

wherein A is an aryl or heteroaryl ring of formula (II) or (III):

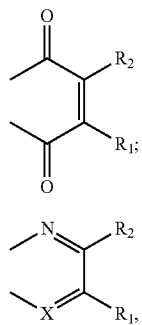

each of $R_1$-$R_6$ is independently selected from the group consisting of H, $NR_7R_8$, $C_{1-10}$ alkyl, and $OR_7$, or $R_1$ and R, combine to form together with the carbon atoms to which they are attached a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$;
X is N or $S^+$;
$R_7$ and $R_8$ are independently selected from the group consisting of H, C(O)—$R_9$, and $C_{1-10}$ Alkyl;
$R_9$ is $C_{1-10}$ Alkyl, under conditions that allow enzymatic cleavage of the covalent bond between the sugar moiety and the redox active reporter moiety and reduction of the redox active report moiety in the presence of the microorganism;

(b) electrochemically determining the released redox active reporter moiety; and (c) determining the presence of the microorganism and, optionally, number of the microorganisms in the sample based on the determined released redox active reporter moiety.

In some embodiments, at least one of $R_1$-$R_6$ is —OH.

The articles "a" and "an" are used herein to refer to one or to more than one (i.e., to at least one) of the grammatical object of the article. By way of example, "an element" means at least one element and can include more than one element.

The term "determine", as used herein, denotes either qualitative or quantitative determination or detection of a microorganism.

The term "microorganism", as used herein, refers to one or more microbes whose presence or number is to be determined. The term may refer to a single microbe (e.g., *Escherichia coli, Enterococcus faecalis, Citrobacter freundii, Staphylococcus aureus, Mycobacterium fortuitum,* and *Klebsiella pneumonia*), a genus of microbes, a number of related species of microbes (e.g., coliforms), or an even larger group of microbes having a common characteristic (e.g., all gram-negative bacteria).

The term "enzyme" is interpreted in its usual way as being a biocatalysator in a cell. In certain embodiments, an enzyme characteristic of the microorganism to be determined is preferred, for example, when there are other microorganisms coexisting in the same sample. The phrase "characteristic of the microorganism", as used herein, means that the expression or activity of an enzyme is exclusive to the target microorganism, or that other microorganisms coexisting in the same sample should not express the enzyme to an extent that the released redox active reporter moiety does no longer appropriately reflect the presence and/or amount of the target microorganism.

The enzymes include all those known to one skilled in the art. Examples include, but are not limited to all the hydrolases listed at http://www.enzyme-database.org/downloads/ec3.pdf.

The term "reporter", as used herein, refers to a sensor that is capable of detecting an event or a parameter that is associated with an event. A parameter associated with an event is any measurable signal that correlates with the occurrence of an event within the frame of reference of the system. The term "electrochemically active reporter" of the present invention refers to a reporter that can respond to a biological event such as cleavage by an enzyme and produce an electrochemical signal.

The term "sugar moiety", as used herein, refers to a sugar group, preferably an aldose, in its cyclic (hemi acetal) form, for example, those derived from furanose (5-membered ring), pyranose (6-membered ring), or oxepanose (7-membered ring). Exemplary of sugar groups include threofuranosyl (from threose, a four-carbon sugar); ribofuranosyl (from ribose, a five-carbon sugar); arafuranosyl (also often referred to as arabinofuranosyl; from arabinose, a five-carbon sugar); xylofuranosyl (from xylose, a five-carbon sugar), lyxofuranosyl (from lyxose, a five-carbon sugar), glucopyranosyl, galactopyranosyl, allopyranosyl, altropyranosyl, mannopyrasonyl, gulopyranosyl, idopyranosyl, and talopyrasonyl. In certain embodiments, the invention contemplates taking advantage of unique enzyme specificities, such as neuraminidase, galactosidase, hyaluronidase and pullulanase, or other characteristics unique to the target microorganism. Thus, the sugar moiety may vary depending upon what microorganisms are present in a sample and which microorganism is selected as the target.

The term "redox active reporter moiety", as used herein, refers to any chemical entity that is inherently capable of electron transfer, and is capable of undergoing a reduction (accepting of an electron) or oxidation (donation of an electron). In the preferred embodiments of the present invention, a redox active reporter moiety is capable of carrying electrons to an electrode. In further preferred embodiments, the redox active reporter moiety is capable of undergoing biological redox reactions mediated by the microorganism to be determined.

The term "alkyl" as used herein refers to a linear, branched, or cyclic saturated hydrocarbon group. The term "$C_{1-10}$ Alkyl" indicates that the group may have from 1 to 10 (inclusive) carbon atoms in it. Examples of $C_{1-10}$ Alkyl groups include, but are not limited to, methyl, ethyl, propyl, isopropyl, 2-methyl-1-propyl, 2-methyl-2-propyl, 2-methyl-I-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, cyclohexyl, heptyl, octyl, nonyl and decyl.

The term "aryl", as used herein, refers to an aromatic ring wherein each of the atoms forming the ring is a carbon atom. The term "heteroaryl" refers to an aromatic heterocycle. The term "alicyclic" refers to a group comprising a non-aromatic ring wherein each of the atoms forming the ring is a carbon atom.

In embodiments where X is $S^+$, the compound can further comprise a suitable anion, preferably an organic anion, such as acetate.

In various embodiments the redox active reporter moiety is selected from the group consisting of 2-hydroxy-1,4-naphthoquinone (2H14NQ), 5-hydroxy-1,4-naphthoquinone (5H14NQ), 5,8-dihydroxy-1,4-naphthoquinone (58H14NQ) and resorufin. It is understood that to form the electrochemically active reporter said redox active reporter moieties are typically covalently coupled to the sugar moiety, for example by means of the oxygen atom of the hydroxyl group.

In various embodiments of the method, the method is carried out by a 3-electrode electrochemical system or a 2-electrode self-powering bioelectrochemical system comprising a working electrode and an electrolyte. According to the present invention, the released redox active reporter moiety can diffuse in an electrolyte to an electrode of said systems and donate an electron thereto to induce an electrical current or voltage. An electrode is the component in an electrochemical system or bioelectrochemical system in contact with the electrolyte medium through which current can flow by electronic movement. Electrodes can be composed of a number of electrically conductive materials, e.g., lead, zinc, aluminum, copper, iron, nickel, mercury, graphite, gold, or platinum. The electrode that is monitored to determine the amount of electrical signal generated at the surface thereof is the "working electrode" sometimes referred to as an "anode" in self-powering bioelectrochemical systems.

The electrolyte medium can be any substance that provides ionic conductivity, and through which the redox active reporter moiety can diffuse. Electrolytes can be solid, liquid, or semisolid (e.g., in the form of a gel). In bioelectrochemical detection of organisms the electrolyte must contain some or all of the necessary components to sustain the organism including, but not limited to, a carbon and nitrogen source along with trace elements. The 3-electrode electrochemical system of the present invention further comprises a reference electrode and a counter electrode. A counter electrode is an electrode used in a three-electrode electrochemical cell for electrochemical analyses in which an electrical current is expected to flow in order to balance the current observed at the working electrode, while the reference electrode is a half-cell of known reduction potential and establishes the electrical potential against which other potentials may be controlled.

The 2-electrode self-powering bioelectrochemical system of the present invention, instead of using an external power source, utilises oxidation/reduction reactions so as to operate as a sensing device. The advantages of a self-powering bioelectrochemical system are numerous, inter alia: (a) as no potential is applied on the electrode, the operation of the detector is specific and it is not interfered by contaminants; (b) since it does not produce voltage in the absence of the substrate, one concentration of the substrate is enough to calibrate the system.

In preferred embodiments of the method, step (a) of the method comprises adding the sample and an effective amount of the electrochemically active reporter to the electrolyte.

The term "effective amount" is an amount within the range which produces an electrical signal detectable by the electrochemical system or the bioelectrochemical system. That is, an amount which allows the target microorganism to cleave sufficient amount of the sugar moiety so as to release sufficient amount of the redox active reporter moiety for the detection. It is not meant to be specific and may vary depending upon such factors as the concentration and activity of the target microorganism.

In preferred embodiments of the method, step (b) comprises measuring the electrical current or voltage resulting from the released redox active reporter moiety by chronoamperometry, potentiometry, voltammetry or other standard electrochemical analyses using the electrochemical system or by determining the potential difference across the electrodes in the bioelectrochemical system.

The term "chronoamperometry", as used herein, relates to an electrochemical measuring technique in which the potential of the working electrode is stepped and the resulting current from faradaic processes occurring at the electrode (caused by the potential step) is monitored as a function of time. The term "voltammetry", as used herein, relates to the determination of current as a function of applied potential and is used to determine the half-cell reactivity of an analyte by contacting it with a working electrode in relation to a reference electrode with a known potential. The term "potentiometry" refers to any technique used to determine the potential between two electrodes.

It is to be understood that the released redox active reporter moiety is oxidized by interaction with the working electrode, and the oxidized released redox active reporter is reduced and reactivated by the microorganism and recycled for the generation of electrical signal. In this context, the electrical signal may result from the combined activity of the released redox active reporter moiety and the target organism.

In preferred embodiments of the method, step (c) comprises determining the number of the microorganisms in the sample based on the electrical signal measured by comparing it to a predetermined standard curve.

The term "standard curve" denotes a relational function indicating a number of microorganisms according to electrical signal values. It may be generated using microorganisms cultured in the laboratory, or preferably using target microorganisms from the same source of samples to be determined.

It is to be understood that said standard curve can be determined from the concentration of the released redox active reporter moiety or from another relationship arising from the combined activity of the target microorganism and the electrochemically active reporter moiety, for example the delay in electrochemical signal onset is directly correlated with the number of the microorganism cells in a sample.

In another embodiment of the method, the target microorganism is allowed to recover from dormancy or stress prior to being subjected to the detection. Microbial dormancy may be common in some samples due to stresses such as starvation, osmotic pressure, and temperature fluctuation. For example, a lag time of growth of approximately 150 min was observed for environmental bacteria compared with laboratory samples. As dormant cells are metabolically compromised and usually show a low enzymatic activity, recovering the target microorganism from dormancy prior to subjecting them to detection, for example, by incubating the sample at a favourable temperature, may reduce the time needed for the detection.

In another embodiment of the method, the microorganism is filtered or concentrated prior to being subjected to the detection.

In another embodiment of the method, an agent is added to the sample to suppress microorganisms other than the target microorganism to be determined. Examples include antifungals such as amphotericin and rosolic acid to suppress Enterobacteriacea that grow at 44.5° C. (e.g. *Staphylococcus aureus*); and cephalosporins such as cefsulodin that selectively inhibit Aeromonads. In certain embodiments, in order to detect coliform bacteria, a bile acid or desoxycholic acid which inhibits growth of microorganisms other than coliform bacteria may be added.

In preferred embodiments of the method, the sugar moiety is a sugar moiety, preferably a pyranose moiety, preferably selected from the group consisting of β-D-glucopyranoside, β-D-galactopyranoside and β-D-glucuronide, and methyl ester, peracetylated and peracetylated methyl ester derivatives thereof.

The term "pyranose moiety", as used herein, refers to a sugar molecule with a pyranose ring.

In preferred embodiments of the method, the electrochemically active reporter is selected from the group consisting of resorufin-β-D-glucopyranoside, methyl ester resorufin-β-D-glucopyranoside, peracetylated resorufin-β-D-glucopyranoside, peracetylated methyl ester resorufin-β-D-glucopyranoside, resorufin-β-D-galactopyranoside, methyl ester resorufin-β-D-galactopyranoside, peracetylated resorufin-β-D-galactopyranoside, peracetylated methyl ester resorufin-β-D-galactopyranoside, resorufin-β-D-glucuronide, methyl ester resorufin-β-D-glucuronide, peracetylated resorufin-β-D-glucuronide, peracetylated methyl ester resorufin-β-D-glucuronide, 2-hydroxy-1,4-naphthoquinone-β-D-glucopyranoside, methyl ester 2-hydroxy-1,4-naphthoquinone-β-D-glucopyranoside, peracetylated 2-hydroxy-1,4-naphthoquinone-β-D-glucopyranoside, peracetylated methyl ester 2-hydroxy-1,4-naphthoquinone-β-D-glucopyranoside, 2-hydroxy-1,4-naphthoquinone-β-D-galactopyranoside, methyl ester 2-hydroxy-1,4-naphthoquinone-β-D-galactopyranoside, peracetylated 2-hydroxy-1,4-naphthoquinone-β-D-galactopyranoside, peracetylated methyl ester 2-hydroxy-1,4-naphthoquinone-β-D-galactopyranoside, 2-hydroxy-1,4-naphthoquinone-β-D-glucuronide, methyl ester 2-hydroxy-1,4-naphthoquinone-β-D-glucuronide, methyl ester 2-hydroxy-1,4-naphthoquinone-β-D-glucuronide, peracetylated 2-hydroxy-1,4-naphthoquinone-β-D-glucuronide, peracetylated methyl ester 2-hydroxy-1,4-naphthoquinone-β-D-glucuronide, 5-hydroxy-1,4-naphthoquinone-β-D-glucopyranoside, methyl ester 5-hydroxy-1,4-naphthoquinone-β-D-glucopyranoside, peracetylated 5-hydroxy-1,4-naphthoquinone-β-D-glucopyranoside, peracetylated methyl ester 5-hydroxy-1,4-naphthoquinone-β-D-glucopyranoside, 5-hydroxy-1,4-naphthoquinone-β-D-galactopyranoside, methyl ester 5-hydroxy-1,4-naphthoquinone-β-D-galactopyranoside, peracetylated 5-hydroxy-1,4-naphthoquinone-β-D-galactopyranoside, peracetylated methyl ester 5-hydroxy-1,4-naphthoquinone-β-D-galactopyranoside, 5-hydroxy-1,4-naphthoquinone-β-D-glucuronide, methyl ester 5-hydroxy-1,4-naphthoquinone-β-D-glucuronide, peracetylated 5-hydroxy-1,4-naphthoquinone-β-D-glucuronide, peracetylated methyl ester 5-hydroxy-1,4-naphthoquinone-β-D-glucuronide, 5,8-dihydroxy-1,4-naphthoquinone-β-D-glucopyranoside, methyl ester 5,8-dihydroxy-1,4-naphthoquinone-β-D-glucopyranoside, peracetylated 5,8-dihydroxy-1,4-naphthoquinone-β-D-glucopyranoside, peracetylated methyl ester 5,8-dihydroxy-1,4-naphthoquinone-β-D-glucopyranoside, 5,8-dihydroxy-1,4-naphthoquinone-3-D-galactopyranoside, methyl ester 5,8-dihydroxy-1,4-naphthoquinone-β-D-galactopyranoside, peracetylated 5,8-dihydroxy-1,4-naphthoquinone-β-D-galactopyranoside, peracetylated methyl ester 5,8-dihydroxy-1,4-naphthoquinone-3-D-galactopyranoside, 5,8-dihydroxy-1,4-naphthoquinone-β-D-glucuronide, methyl ester 5,8-dihydroxy-1,4-naphthoquinone-β-D-glucuronide, peracetylated 5,8-dihydroxy-1,4-naphthoquinone-β-D-glucuronide, and peracetylated methyl ester 5,8-dihydroxy-1,4-naphthoquinone-β-D-glucuronide.

The term "peracylated" or "acetylated", as used herein, means that all or some of the hydroxyl groups of the corresponding unprotected compound have been converted to an acetyl group ($C(O)CH_3$); where not all the functional groups on the sugar moiety, such as a carboxyl group, are acetylated and at least one functional group is a methyl ester ($C(O)OCH_3$), in the instance herein the carboxyl group at C6, the term "peracetylated methyl ester" is used.

In the method, the covalent bond between the sugar moiety and the redox active reporter moiety is cleaved by an enzyme expressed by the microorganism to be determined. Said cleavage of the bond may occur upon recognition and binding of the sugar moiety by an enzyme. Said cleavage releases the redox active reporter moiety which can then subsequently be electrochemically detected. It is preferred in various embodiments of the invention that the electrochemically active reporter in its non-cleaved form is either not detectable by the method or its signal is clearly distinguishable from that of the released report moiety to allow specific and sensitive detection of the microorganism in a sample.

While the enzyme facilitating release of the redox active report moiety may be expressed constitutively, in various embodiments of the method, the enzyme is an inducible enzyme and expression of the respective enzyme is induced. Such inducers may include, but are not limited to, isopropyl-β-D-thiogalactoside (IPTG) which induces β-D-galactosidase activity, ethyl-β-D-thioglucoside which induces β-glucosidase activity, and methyl β-D-glucuronide which induces β-D-glucuronidase activity.

Once the covalent bond between the sugar moiety and the redox reporter is cleaved, the redox reporter can diffuse out of the cells or be actively secreted. In general, uptake of the redox reporter into the cell leads to reduction of the reporter due to the reducing environment in the interior of the cell.

In certain embodiments of the method, the method further comprises a step of lysing the cell membrane or enhancing membrane permeability of the microorganism to facilitate the release of the redox active reporter moiety or the enzyme cleaving the electrochemically active reporter. It may be achieved by contacting them with an organic solvent such as toluene, chloroform, lytic enzymes (e.g. lysozyme), or by a physical method such as a sonic disintegration using ultrasound or by passing the culture through a homogenizer using shear forces to lyse the cells.

The electrochemically active reporter conjugate may be actively transported into the cells by targeting a transporter or transmembrane channel or may passively diffuse into the cells. Depending on the properties of the reporter conjugate, lysis of the cells or permeation of the membrane may be necessary to facilitate the contact between the enzyme of the target microorganism used for cleavage and detection, for example by using the above described methods. Similarly, release of the cleaved reporter moiety from the interior of the cells may be facilitated by the same lysis or permeation methods.

In certain embodiments of the method, the method is a multiplex method that allows simultaneous determination of a number of different organisms. In such methods, for each microorganism to be detected a different electrochemically active reporter may be used to allow simultaneously determining a number of different microorganisms. Development of a genuine multiple-organism detection system may involve the development of a plurality of electrochemically active reporters whose redox active reporter moieties each have a different redox potential. The system may contain multiple electrodes each having a different redox poise (the potential at which they can be reduced by the redox active reporter moieties) to selectively discriminate against the different organisms present. To be truly selective the redox poise of each electrode will need to be both within a biologically relevant range but sufficiently different from one another to prevent unpredictable cross talk. The redox poise of the electrode will need to be controlled, and whilst this can take advantage of the natural properties of the electrode, it will likely require the incorporation of simple resistors or potentiostatic capability into the device. Another more advanced refinement can be achieved by surface treating electrodes with the electrochemically active reporters meaning that it will only be activated by the target organism.

In various embodiments of the method, the sample is an environmental or biological sample. For example, the sample can be from recreational or potable water, or form a laboratory or the food industry.

In preferred embodiments of the method, the microorganism is a coliform bacterium. The term "coliform bacterium", as used herein, refers to a group of bacterial genera made up of *Escherichia, Klebsiella, Enterobacter, Serratia* and *Citrobacter* bacteria. Coliform bacteria tend to be small, gram negative rods that may be either motile or nonmotile.

In one preferred embodiment of the method, the microorganism is *Escherichia coli,* the enzyme expressed by the microorganism is β-glucuronidase, and the sugar moiety is β-D-glucuronide. The enzyme β-D-glucuronidase catalyzes the hydrolysis of the O-glycosyl bond in β-D-glucuronosides with the release of D-glucuronic acid. The enzyme is found in most vertebrates and many molluscs, but is generally absent in higher plants, mosses, algae, ferns, fungi, as well as in most bacteria. It is often used as a general marker for total coliforms. Thus, the activity of this enzyme can be used as an indicator of fecal pollution and to determine the number of bacteria.

In another preferred embodiment of the method, the microorganism is *Escherichia coli,* the enzyme expressed by the microorganism is β-D-galactosidase, and the sugar moiety is β-D-galactopyranoside.

In certain embodiment of the method, the microorganism is *Escherichia coli,* the enzyme expressed by the microorganism is β-glucosidase, and the sugar moiety is β-D-glucopyranoside.

In yet another preferred embodiment of the method, the microorganism is *Enterococcus faecalis,* the enzyme expressed by the microorganism is β-glucosidase and the sugar moiety is β-D-glucopyranoside.

In some embodiments, the microorganism is *Streptococcus pneumonia, Pseudomonas aeruginosa, Vibrio cholera* or *Shigella dysenteriae* and the enzyme expressed by the microorganism is neuraminidase, the microorganism is a *Streptococcus* species (e.g. *S. aureus, delphinii, hyicus, intermedius, lutrae, schleiferi* or *pseudintermedius*) and the enzyme expressed by the microorganism is Hyaluronidas, or the microorganism is *Klebsiella pneumonia* and the enzyme expressed by the microorganism is Pullulanase. Possible sugar moieties such as N-acetylneuraminic acid and N-acetylglucosamine are known in the art.

The invention also encompasses an electrochemically active reporter for determining the presence of a microorganism in a sample, wherein the electrochemically active reporter is a conjugate comprising a sugar moiety and a redox active reporter moiety that are covalently linked such that the covalent bond can be enzymatically cleaved in the presence of the microorganism by an enzyme expressed by the microorganism, wherein the redox active reporter moiety is selected from the group consisting of resorufin and compounds of formula (I)

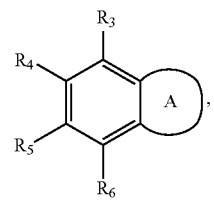

(I)

wherein A is an aryl or heteroaryl ring of formula (II) or (III):

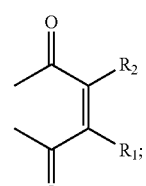

(II)

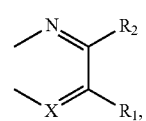

(III)

each of $R_1$-$R_6$ is independently selected from the group consisting of H, $NR_7R_8$, $C_{1-10}$ alkyl, and $OR_7$, or $R_1$ and $R_2$ combine to form together with the carbon atoms to which they are attached a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$;

X is N or $S^+$;

$R_7$ and $R_8$ are independently selected from the group consisting of H, C(O)—$R_9$, and $C_{1-10}$ Alkyl;

$R_9$ is $C_{1-10}$ Alkyl.

In various embodiments of the electrochemically active reporter, the redox active reporter moiety is electrochemically reversible.

The term "electrochemically reversible", as used herein, means that a molecule or substance has electrochemically reversible behaviour and can gain and lose electrons repeatedly without its electrochemical profile varying over time.

In various preferred embodiments of the electrochemically active reporter, the redox active reporter moiety is selected from the group consisting of 2-hydroxy-1,4-naphthoquinone, 5-hydroxy-1,4-naphthoquinone and 5,8-dihydroxy-1,4-naphthoquinone or resorufin.

In various preferred embodiments of the electrochemically active reporter, the sugar moiety is a pyranose moiety, preferably selected from the group consisting of β-D-galactopyranoside, β-D-glucuronide and β-D-glucopyranoside and methyl ester, peracetylated and peracetylated methyl ester derivatives thereof.

In various preferred embodiments of the electrochemically active reporter, the electrochemically active reporter is selected from the group consisting of resorufin-β-D-glucopyranoside, methyl ester resorufin-β-D-glucopyranoside, peracetylated resorufin-β-D-glucopyranoside, peracetylated methyl ester resorufin-β-D-glucopyranoside, resorufin-β-D-galactopyranoside, methyl ester resorufin-β-D-galactopyranoside, peracetylated resorufin-β-D-galactopyranoside, peracetylated methyl ester resorufin-β-D-galactopyranoside, resorufin-β-D-glucuronide, methyl ester resorufin-β-D-glucuronide, peracetylated resorufin-β-D-glucuronide, peracetylated methyl ester resorufin-β-D-glucuronide, 2-hydroxy-1,4-naphthoquinone-β-D-glucopyranoside, methyl ester 2-hydroxy-1,4-naphthoquinone-β-D-glucopyranoside, peracetylated 2-hydroxy-1,4-naphthoquinone-β-D-glucopyranoside, peracetylated methyl ester 2-hydroxy-1,4-naphthoquinone-β-D-glucopyranoside, 2-hydroxy-1,4-naphthoquinone-β-D-galactopyranoside, methyl ester 2-hydroxy-1,4-naphthoquinone-β-D-galactopyranoside, peracetylated 2-hydroxy-1,4-naphthoquinone-β-D-galactopyranoside, peracetylated methyl ester 2-hydroxy-1,4-naphthoquinone-β-D-galactopyranoside, 2-hydroxy-1,4-naphthoquinone-β-D-glucuronide, methyl ester 2-hydroxy-1,4-naphthoquinone-β-D-glucuronide, methyl ester 2-hydroxy-1,4-naphthoquinone-β-D-glucuronide, peracetylated 2-hydroxy-1,4-naphthoquinone-β-D-glucuronide, peracetylated methyl ester 2-hydroxy-1,4-naphthoquinone-β-D-glucuronide, 5-hydroxy-1,4-naphthoquinone-β-D-glucopyranoside, methyl ester 5-hydroxy-1,4-naphthoquinone-β-D-glucopyranoside, peracetylated 5-hydroxy-1,4-naphthoquinone-β-D-glucopyranoside, peracetylated methyl ester 5-hydroxy-1,4-naphthoquinone-β-D-glucopyranoside, 5-hydroxy-1,4-naphthoquinone-β-D-galactopyranoside, methyl ester 5-hydroxy-1,4-naphthoquinone-β-D-galactopyranoside, peracetylated 5-hydroxy-1,4-naphthoquinone-β-D-galactopyranoside, peracetylated methyl ester 5-hydroxy-1,4-naphthoquinone-β-D-galactopyranoside, 5-hydroxy-1,4-naphthoquinone-β-D-glucuronide, methyl ester 5-hydroxy-1,4-naphthoquinone-β-D-glucuronide, peracetylated 5-hydroxy-1,4-naphthoquinone-β-D-glucuronide, peracetylated methyl ester 5-hydroxy-1,4-naphthoquinone-β-D-glucuronide, 5,8-dihydroxy-1,4-naphthoquinone-β-D-glucopyranoside, methyl ester 5,8-dihydroxy-1,4-naphthoquinone-β-D-glucopyrano side, peracetylated 5,8-dihydroxy-1,4-naphthoquinone-β-D-glucopyranoside, peracetylated methyl ester 5,8-dihydroxy-1,4-naphthoquinone-β-D -glucopyrano side, 5,8-dihydroxy-1,4-naphthoquinone-β-D-galactopyranoside, methyl ester 5,8-dihydroxy-1,4-naphthoquinone-β-D-galactopyranoside, peracetylated 5,8-dihydroxy-1,4-naphthoquinone-β-D-galactopyranoside, peracetylated methyl ester 5,8-dihydroxy-1,4-naphthoquinone-β-D-galactopyranoside, 5,8-dihydroxy-1,4-naphthoquinone-β-D-glucuronide, methyl ester 5,8-dihydroxy-1,4-naphthoquinone-β-D-glucuronide, peracetylated 5,8-dihydroxy-1,4-naphthoquinone-β-D-glucuronide, and peracetylated methyl ester 5,8-dihydroxy-1,4-naphthoquinone-β-D-glucuronide. A skilled artisan, based on the present disclosure and the common general knowledge, is able to select an enzyme, a sugar moiety and a redox active reporter moiety in order to make an electrochemical reporter of the present invention such as to electrochemically determine the presence of a microorganism expressing the enzyme.

The electrochemically active reporters may be produced by methods well known to those of skill in the art.

In still another aspect, the invention encompasses use of an electrochemically active reporter comprising a sugar moiety and a redox active reporter moiety that are covalently linked such that the covalent bond can be enzymatically cleaved in the presence of a microorganism by an enzyme expressed by the microorganism for determination of the presence of said microorganism in a sample, wherein the redox active reporter moiety is selected from the group consisting of resorufin and compounds of formula (I)

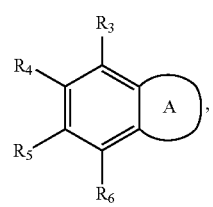

(I)

wherein A is an aryl or heteroaryl ring of formula (II) or (III):

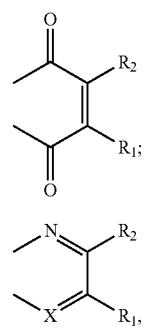

(II)

(III)

each of $R_1$-$R_6$ is independently selected from the group consisting of H, $NR_7R_8$, $C_{1-10}$ alkyl, and $OR_7$, or $R_1$ and $R_2$ combine to form together with the carbon atoms to which they are attached a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$; X is N or $S^+$; $R_7$ and $R_8$ are independently selected from the group consisting of H, C(O)—$R_9$, and $C_{1-10}$ Alkyl;

$R_9$ is $C_{1-10}$ Alkyl.

The present invention is further illustrated by the following examples. However, it should be understood, that the invention is not limited to the exemplified embodiments.

EXAMPLES

Example 1

Electrochemically Active Reporters

Resorufin (TCI-Europe), 2-hydroxy-1,4-naphthoquinone (2H14NQ) (TCI-Europe), 5-hydroxy-1,4-naphthoquinone (5H14NQ) (TCI-Europe) and 5,8-dihydroxy-1,4-naphthoquinone (58H14NQ) (Sigma-Aldrich) were obtained commercially and added to M9 medium in their unconjugated form to achieve a working concentration of 50 μM. Resorufin glycoconjugates (resorufin-β-d-galactopyranoside and resorufin-β-d-glucopyranoside) were obtained commercially (Sigma-Aldrich), whereas 2-hydroxy-1,4-naphthoquinone-β-d-galactopyranoside (2H14NQGal) and 2-hydroxy-1,4-naphthoquinone-β-d-glucopyranoside (2H14NQGlu) were specifically synthesized by Sussex Research Ltd. All reporters were added to a final concentration of 50 μM. Stock concentrations ($1.0×10^{-3}$ M) of 2H14NQ and 5H14NQ were prepared by first dissolving in 10 μL of 2 M NaOH and then making up to volume in Type II water (Veolia) whereas 58H14NQ ($1.0×10^{-3}$ M) was prepared in 1:1 DMSO:Type II water aliquots. Both stock solutions were stored at −20° C. until needed. Conjugated reporters were maintained as 1 mM stock solutions in Type II water and stored at 5° C.

Example 2

Microorganism and Growth Conditions

*Escherichia coli* strain BL21 was selected to represent a FIB of human origin that contains the uidA and lacZ genes, i.e. a FC, whereas *Aeromonas hydrophila* (DSM 6173) is an environmental organism that has the lacZ gene but which is not considered a coliform. All organisms were cultured aerobically for 20 h. *E. coli* was grown in Luria Bertani (Lennox) medium at 37° C., and *A. hydrophile* at 30° C. in tryptone soy broth (TSB) in a shaking incubator.

The resulting overnight cultures were diluted in sterile modified M9 medium ($Na_2HPO_4.7H_2O$ (126 mM); $KH_2PO_4$ (110 mM); $NH_4Cl$ (93 mM); NaCl (42 mM); 1 mL/L vitamin stock solution; tryptone 12.5 g/L; HEPES: 6 g/L; and macro nutrients). The carbon source was either D-galacturonic acid or D-glucuronic acid (3.75 g/L) to achieve a final inoculum density in the range of $1.0×10^0$, $5.0×10^0$, $5.0×10^1$, $5.0×10^2$, $5.0×10^3$, $5.0×10^4$, and $5.0×10^5$ CFU $mL^{-1}$ in both electrochemical system and the bioelectrochemical system.

Example 3

Construction of Electrochemical Systems (ECs)

Conical ECs with a working volume of 10 mL were used with a customized Teflon cap to accommodate a three electrode configuration along with gas fittings to maintain a moist anaerobic atmosphere. Carbon felt working electrodes (1×1×0.318 cm) (VWR, Singapore) were kept for 24 h in 1 M HCl and stored in deionized (DI) water before use. The electrodes were connected to titanium wire (0.25 mmØ, Sigma-Aldrich) using a nylon nut and bolt. A coiled titanium wire was used as counter electrode and an Ag/AgCl reference electrode (78 mm, 6 mm Outer Ø, Biologic, France) was connected using a 1 M KCl in 1.5% agar salt bridge. The assembled cell was then filled with 1 M KCl solution ending in a 4 mm glass frit (CoralPor™, Biologic, France). The entire assembly was then autoclaved (121° C. for 15 min). Nine mL of degassed modified M9 medium was added to the ECs and supplemented with a reporter to a final concentration of $5.0×10^{-5}$ M in 10 mL working volume. The ECs were then inoculated with the targeted test organism to achieve a final working volume of 10 mL. The headspace was flushed continuously with sterile humidified $N_2$. The ECs were operated at 30° C., 37° C. or 44.5° C. Stirring was maintained continuously with a magnetic stirrer in the dark to prevent photo-bleaching of the light sensitive mediators.

Example 4

Electrochemical Data Acquisition using ECs

Following reporter supplement and inoculation with the test microorganism, the ECs were connected to a multichannel potentiostat (Biologic, France) and cyclic voltammetry (CV) and differential pulse voltammetry (DPV) were performed immediately. Data acquisition was recorded by EC-Lab software (Biologic, France). Chronoamperometry (CA) was applied for up to 24 h to detect redox active reporter moieties. A detection event was calculated as 4 times the standard deviation of the baseline and detection times are expressed as the mean of triplicate analyses unless stated otherwise.

The parameters for the electrochemical techniques were chosen accordingly:
CA: $E_{applied}$=200 mV vs Ag/AgCl
CV: equilibrium time of 5 s; scan rate of 10 mV/s; $E_i$=−700 mV vs Ag/AgCl; $E_f$=500 mV vs Ag/AgCl
DPV: $E_i$=−700 mV vs Ag/AgCl; $E_f$=500 mV vs Ag/AgCl; pulse height of 50 mV; pulse width of 200 ms; step height of 2 mV; step time of 400 ms; scan rate of 5 mV/s.

Example 5

Construction of Bioelectrochemical Systems (BESs)

Dual chamber U-tube BESs, in the form of microbial fuel cells (MFCs), were constructed with two 90° 28/15 ball-to-plain-end and socket-to-plain-end glass quick fit elbows (17 mm O.D.×1.8 mm wall thickness) (VWR, Singapore) to form the anode and cathode chambers (Sund et al., Appl. Microbiol. Biotechnol. 2007; 76:561-568.). Both chambers were separated by a Nafion® N117 (Ion Power, USA) proton exchange membrane (PEM). Carbon felt electrodes (5×2×0.318 cm) (VWR, Singapore) were used in both chambers and connected to a titanium wire using nylon screws and nuts. Both chambers were held together with a 28/15 stainless steel pinch clamp (#28) (VWR, Singapore) and high-vacuum silicone grease. A serrated silicone septum (Z512877, 18 mm outer Ø) (Sigma Aldrich, Singapore) was used to seal the anode chamber. The cathode chamber was covered loosely with a glass vial to allow for aerobic condition. In the anode chamber, the electrode was completely submerged in media which was supplemented to $5\times10^{-5}$ M final reporter concentration and inoculated with *E. coli*. The cathode was partly submerged (~50% surface area) in an 'air-wicking' aerobic configuration (18). A 1 kΩ load was applied across the circuit and potential difference was recorded using an eDAQ e-corder® data acquisition system (ED 1621-16 channel recorder) equipped with Chart™ software (Bronjo Medi, Singapore) at a rate of 1 data point every 5 min. The BES were operated at ambient temperature (Wang et al., Phys. Chem. Chem. Phys. 2013; 15:5867-5872.)

Example 6

Electrochemical Determination of Microorganisms

Figure 2:
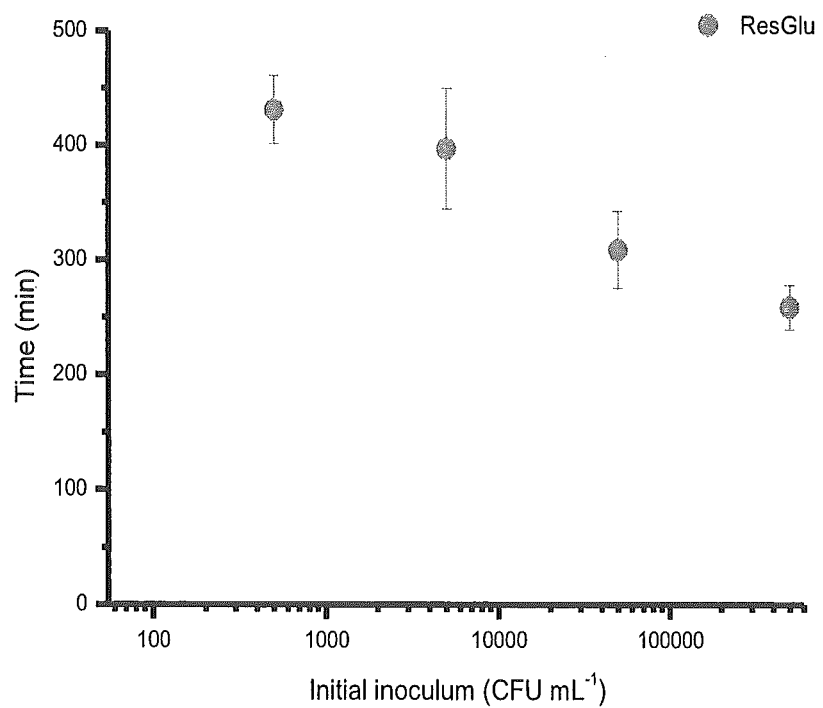
FIG. 2 shows a plot of the detection time for different inoculum sizes of E. coli incubated at 37° C. with an electrochemically active reporter, Resorufin-β-D-glucopyranoside (resglu), based on chronoamperometry. (Error bars±1×standard deviation, n=3).

The ability of a range of microorganisms to reduce resorufin is well documented and the reversible nature of this reaction has utility as a redox dye in anaerobic microbiology to indicate the redox status of a medium, when it turns from colourless to pink at a redox potential above ~−50 mV Commercial resorufin glycoconjugates make excellent candidate reporters which can be employed in bioelectroanalytical systems to detect of *E. coli* in ECs (FIG. 2). Detection of *E. coli* was achieved with resorufin-β-d-galactopyranoside (ResGal) as an electrochemically active reporter in ECs in 4-10 h for inoculum sizes ranging between $5\times10^5$ and $5\times10^3$ CFU mL$^{-1}$ with good reproducibility across triplicate analysis (FIG. 2). The detection time reported by Perez et al. for *E. coli* which were not induced with Isopropyl β-D-1-thiogalactopyranoside (IPTG) and for an equivalent inoculum size of $5\times10^3$ CFU mL$^{-1}$ was ~6.5 h. This is faster than the detection time of ~8 h reported here for ResGal (Table 1) but comparable with the detection time of 6.6 h that was achieved for ResGlu (FIG. 2). Detection times for colourimetric β-glucuronidase assays have been reported to be as low as 0.5 h and 5 h with higher sensitivity (1 CFU mL$^{-1}$) but these techniques require several pretreatment steps, such as filtration pre-incubation, staining and specialist detection equipment. The saving in time is offset by concomitant increase in manpower or complexity, effectively making these approaches labour intensive and laboratory based (Nelis and Van Poucke, Environmental Challenges. 2000 Springer; Fiksdal et al., Appl. Environ. Microbiol. 1994; 60:1581-1584). While the sensitivity of these rapid techniques is undeniably high (detecting 4-APGAl in quantities as low as 45 ng/L), the quantification step is usually carried out under alkaline conditions to maximize the optical properties of aglycon, further complicating the procedure. Despite these apparent advances, the detection time for commercial, regulatory approved *E. coli* detection methods is in the range 18-28 h for drinking water applications.

TABLE 1

Summary of the detecton times for *E. coli* with inoculum sizes of $5\times10^2$, $5\times10^3$, $5\times10^4$, $5\times10^5$ CFU mL$^{-1}$ achieved with two commercially available glycoconjugate detection compounds (ResGlu and ResGal) and two compounds described for the first time in this study (2H14NQGal and 2H14NQGlu). Detection time is calculated from chronoamperometry performed in ECs and expressed as the mean detection time in minutes (error bars = ±1x standard deviation, n = 3 except * where n < 3).

Detection time (±std dev)

| | Temperature | | | | | |
| --- | --- | --- | --- | --- | --- | --- |
| | 30° C. | | 37° C. | | | |
| CFU mL$^{-1}$ | ResGal | 2H14NQGlu | ResGal | ResGlu | 2H14NQGal | 2H14NQGlu |
| $5\times10^2$ | 521(±121) | 832* | 734(±188) | 431(±29) | 413(±14) | 339(±41) |
| $5\times10^3$ | 372(±82) | 574* | 477(±23) | 397(±52) | 359(±13) | 187(±31) |
| $5\times10^4$ | 218(±31) | n/d | 309(±55) | 309(±33) | 143(±17) | 142(±11) |
| $5\times10^5$ | 150(±56) | 168* | 260 (±55) | 259(±19) | 113(±13) | 120(±21) |

Although resorufin-β-d-galactopyranoside can be used to detect the presence and quantity of *E. coli*, it is expensive with the inventors' source costing over US$3,000 for one gram (23). Glycoconjugate synthesis requires that the carboxyl and alcohol groups are protected during synthesis with a methyl ester and an acetyl group respectively. The deprotection step is problematic and yields can be as low as 5% (European patent application No. EP20110169147; U.S. patent application Ser. No. 09/781,885). To offset the additional cost of the electrode in the proposed electrochemical *E. coli* detection framework, it was reasoned that low-cost electrochemically active reporters would be essential and that cheap, biologically compatible redox active molecules conjugated to peracetylated methyl ester monosaccharides would fulfil this essential criterion. The resulting reporters would benefit from fewer synthetic steps, resulting in increased yields and reduced production costs of up to 95% compared with fully deprotected glycoconjugates, such as res-gal, 4-APgal, and 4-NPglu. As *E. coli* and other coliforms express native esterases, they are biochemically equipped to convert the peracetylated methyl ester glycoconjugates to the acid form in situ if this is necessary for subsequent electrochemical activity (Antonczak et al., J. Biol. Chem. 2009; 284:28795-28800).

Figure 3:
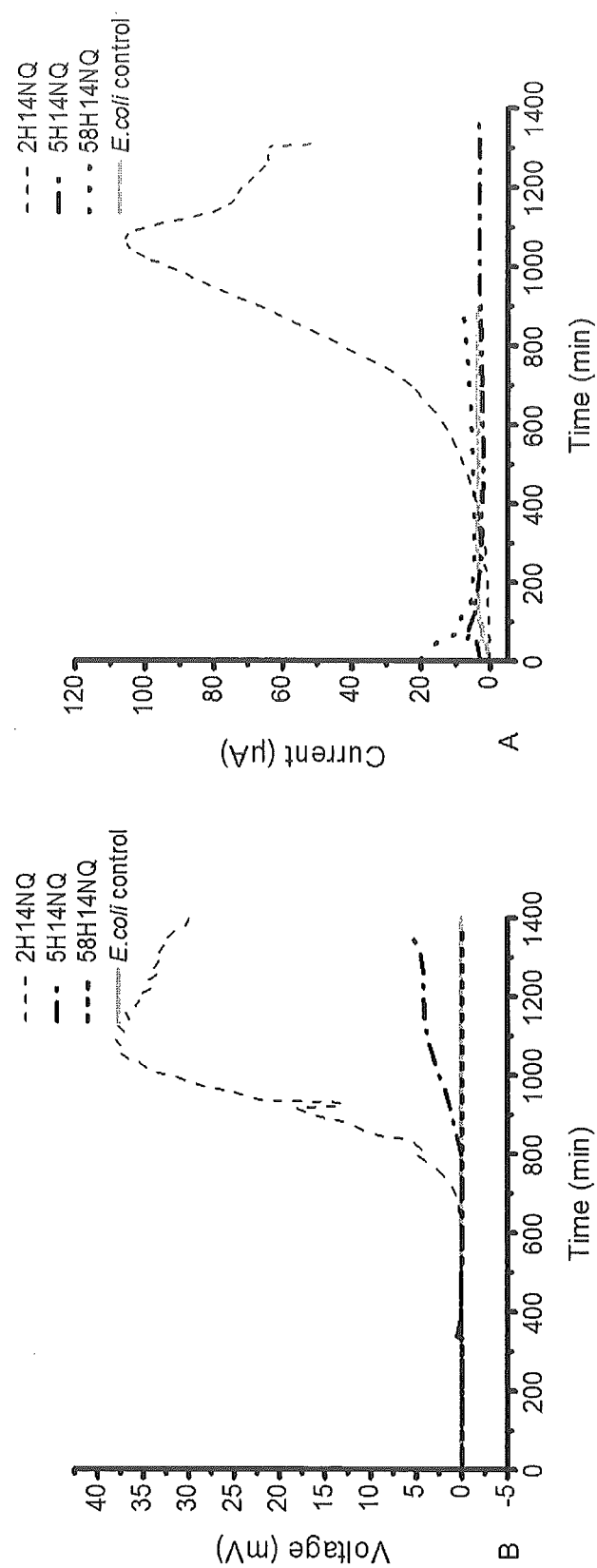
FIG. 3 shows plots of duplicate chronoamperometry (A) and voltage (B) profile of redox active reporters. Note that 2-hydroxy-1,4-naphthoquinone (2H14NQ) outperforms 5-hydroxy-1,4-naphthoquinone (5H14NQ) and 5,8-dihydroxy-1,4-naphthoquinone (58H14NQ) in terms of onset time and maximum voltage, which is sustained over longer periods, despite only minor differences in structure. Note the absence of significant current in the controls incubated with E. coli only.
Figure 4:
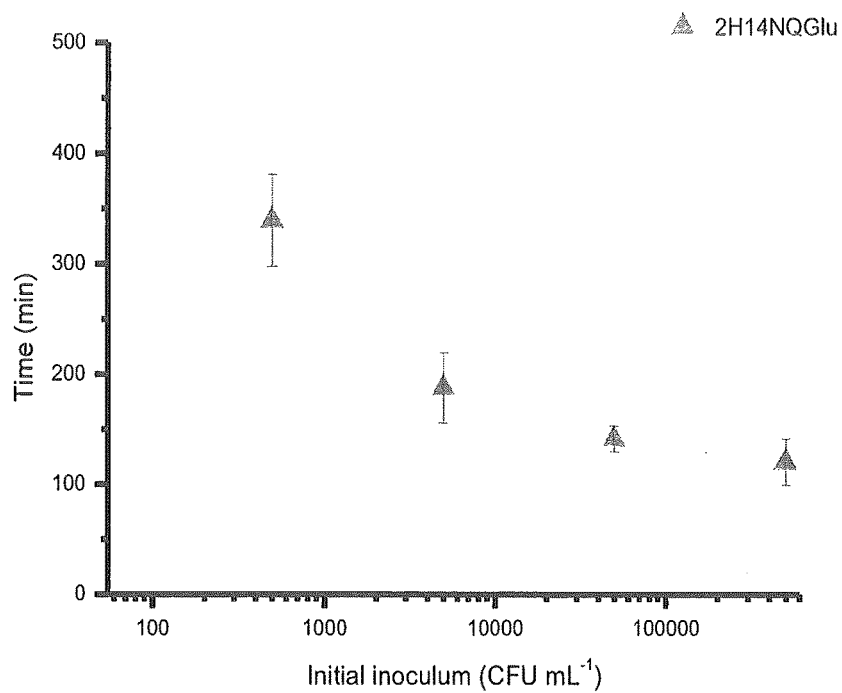
FIG. 4 shows a scatterplot showing detection time for different inoculum sizes of E. coli incubated at 3TC with peracetylated methyl ester 2-hydroxy-1,4-naphthoquinone-O-D-glucopyranoside (2H14NQGlu) based on chronoamperometry. (Error bars±3×standard deviation, n=3).

Naphthoquinones are cheap redox active molecules which are compatible with *E. coli* and can be readily conjugated to pyranose rings (Rau et al. Environ. Sci. Technol. 2002; 36:1497-1504; Park and Zeikus. Appl. Environ. Microbiol. 2000; 66:1292-1297). Their ability to mediate electron transfer between *E. coli* and an electrode in BESs and ECs validates their potential as candidate *E. coli* detection compounds (FIG. 3). Out of three candidate naphthoquinones, i.e. 2-hydroxy-1,4-naphthoquinone (2H14NQ), 5-hydroxy-1,4-naphthoquinone (5H14NQ) and 5,8-dihydroxy-1,4-naphthoquinone (58H14NQ) that we tested, 2H14NQ outperformed both 5H14NQ and 58H14NQ in ECs (FIG. 3). The maximum recorded current in ECs incubated with $5\times10^5$ CFU mL$^{-1}$ of *E. coli* and using 2H14NQ as the redox active reporter moiety was ~100 µA, which was ~14 times the maximum current achieved with 5H14NQ (~7 µA) and ~25 times that observed when 58H14NQ (~4 µA) was used. In BES, the current observed was 40 µA, 6 µA and 2.5 µA for 2H14NQ, 5H14NQ and 58H14NQ respectively, reflecting a similar trend to that observed in ECs. However, the magnitude of difference between 2H14NQ and the other candidate napthoquinones was less pronounced in BESs than ECs was most likely reflecting the absence of a cathodic limitation in the ECs. Accordingly, 2H14NQ was selected for conjugation to both galacturonic acid and glucuronic acid on the basis of its sound electrochemical performance and its potential to enable bioelectroanalytical detection of *E. coli*. The different electrochemical performance of the candidate naphthoquinones was unexpected although it has been previously reported that the electron transfer kinetics are dependent on the stability of intramolecular hydrogen bonds of the various naphthoquinones. There are two types of hydrogen bond systems in the naphthoquinones studied here. 2H14NQ has an a-hydroxy system (where the interaction between the carbonyl group and the hydroxy group is supported on the same ring) while 5H14NQ and 58H14NQ have a β-hydroxy system (where the intramolecular interaction occurs between adjacent rings). Electron transfer kinetics are affected by the β-hydroxy systems and likely underlie the poor bioelectrochemical performance of 5H14NQ and 58H14NQ compared to 2H14NQ.

Example 7

Performance of Novel Electrochemically Active Reporters

Both 2-hydroxy-1-4-napthoquinone β-D-galactopyranoside (2H14NQGal) 2-hydroxy-1,4-naphthoquinone β-D-glueopyranoside (2H14NQGlu) glycoconjugates can be used to detect the presence of *E. coli* in ECs, confirming sound rationale in molecular selection. The detection time for *E. coli* using 2H14NQGlu ranges between 120-188 min (±7.4-17%, n=3) for inoculum sizes between $5 \times 10^5$-$5 \times 10^3$ (Table 1). The detection times achieved with 2H14NQGlu is quicker than that observed for ResGlu (258-397 min) and it compares well to the detection time reported by Perez et al. of ~390 min for $5 \times 10^3$ CFU mL$^{-1}$ (Table 1). However, the value reported by Perez et al. was for a galactopyranoside conjugate, hence a direct comparison is invalid. But the galactopyranoside equivalent (2H14NQGal) used here resulted in only a slightly slower detection time of 412 min (±3.3%, n=3) versus 390 min reported by Perez at al. for an equivalent inoculum size. The naphthoquinone glycoconjugates result in faster detection times than their resorufin glycoconjugate counterparts, demonstrating that the peractelylated methyl ester glycoconjugates offer both cost savings and performance benefits in the context of bioelectroanalytical *E. coli* detection.

Example 8

Applicability of Bioelectroanalytical Approach to Environmental TC Detection

An ideal remote biosensor would have as few components as possible. It was explored the possibility of omitting the heating component of a detection unit and if TC monitoring at ambient Singapore temperatures (~30° C.) was achievable within this framework. The inoculum density of *E. coli* could be correlated well with an electrochemical response of ResGal at 30° C., and the detection times were not particularly impacted (Table 1). In fact, the detection times were slightly quicker for *E. coli*, ranging between 132-521 min for inoculum sizes of $5 \times 10^5$-$5 \times 10^2$ (Table 1).

The common aquatic organism, *A. hydrophila* is a common false positive in water quality monitoring framework that rely on the enzymatic testing of β-galactosidase activity as it is galactosidase positive. However, being telluric rather than enteric origin, it is not considered a coliform (Cabral. International Journal of Environmental Research and Public Health 2010; 7:3657-3703; Waltman et al., J. Clin. Microbiol. 1982; 16:692-696). As *A. hydrophila* could be detected electrochemically with ResGal at both 30° C. and 37° C. (FIG. 5) and because it is reportedly electrogenic (Logan. Nat. Rev. Micro. 2009; 7:375-381), its ability to interfere with TC detection in this framework was investigated in more detail.

Figure 5:
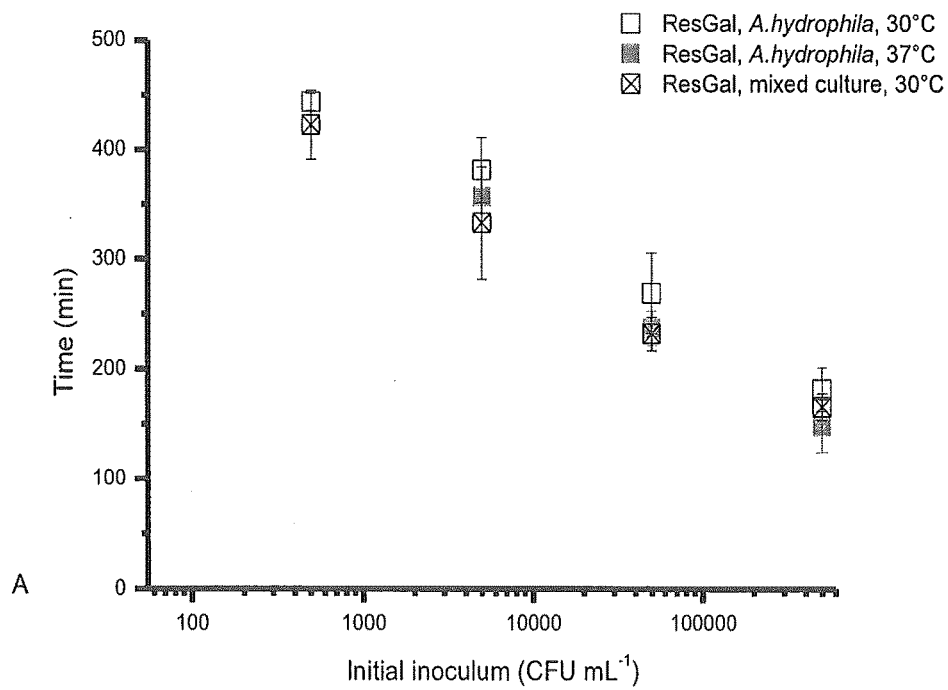
FIG. 5 shows a plot of detection time for different inoculum sizes of A. hydrophila detection at 30 and 37° C. with Resorufin-β-D-galactopyranoside (ResGal), A. hydrophila and E. coli mixed cultures at 30° C. with A. hydrophila at different initial inoculum sizes while the initial inoculum of E. coli is kept at $5.0 \times 10^5$ CFU mL-1 (Error bars±1× standard deviation, n=3).

In a test with a constant inoculum size of *E. coli* ($5 \times 10^5$ CFU mL$^{-1}$) but with an increasing *A. hydrophila* concentration from $5 \times 10^2$ to $5 \times 10^5$ CFU mL$^{-1}$, a decrease in the detection time from ~450 to ~280 min was observed, indicating that *A. hydrophila* strongly influences the detection signal for a mixed culture of *E. coli* and *A. hydrophila* at 30° C. (FIG. 5). Furthermore, the detection time is likely to be dominated by *A. hydrophila* as the similarities of the combined incubation (FIG. 5) are similar to that of a pure culture of *A hydrophila* at 30° C., indicating suppression of *E. coli* by *A. hydrophila* or other competitive interactions (Pham et al., FEMS Microbiol. Lett. 2003; 223:129-134). While interference from coliforms, such as *Kleibsella* spp. and *Citrobacter* spp. is expected for galactosidase enzymatic tests, the inability to differentiate between *E. coli* and *A. hydrophila* means that this technique will overestimate *E. coli* or TCs at ambient temperatures in the presence of hydromonads. Interference from hydromonads is a well-documented shortcoming of enzymatic β-galactosidase detection and 4 commercially available methods exhibited this problem upon testing (Manafi. International Journal of Food Microbiology 2000; 60:205-218). Hydromonad interference can be mitigated by selective medium, specifically the incorporation of inhibitors such as cefsulodin (Manafi. International Journal of Food Microbiology 2000; 60:205-218; Geissler et al., Journal of Applied Microbiology 2000; 88:280-285). The development of such a selective medium is beyond the scope of this contribution. However, in principle, TC quantification is possible with this framework and can be achieved at ambient tropical temperatures with shortcomings similar to what would be expected with more established enzymatic β-galactosidase detection methods with minimal impact on detection times.

Example 9

Applicability of Bioelectroanalytical Approach to FC Detection

Enzymatic tests for β-glucuronidase activity at 44.5° C. are considered a more definitive test for FCs and *E. coli*. It is sometimes referred to as the thermotolerant coliform test because some *Shigella* spp. and *Salmonella* spp. will also detect positive using this method. This apparent lack of specificity has its origins in the historical assignment of these organisms to different genera, based mainly on the pathology of the diseases they cause. However, with modern molecular insights, these taxa would be consigned to the same genus (Lan and Reeves. Microbes and infection 2002; 4:1125-1132). In a test with a constant inoculum size of *E. coli* ($5 \times 10^5$ CFU mL$^{-1}$) but with an increasing inoculum size of *A. hydrophila* (from $5 \times 10^2$-$5 \times 10^5$ CFU mL$^{-1}$) and using 2H14NQGlu as a reporter, the detection time remained constant (125-172 min), indicating the contribution of *A.*

Figure 6:
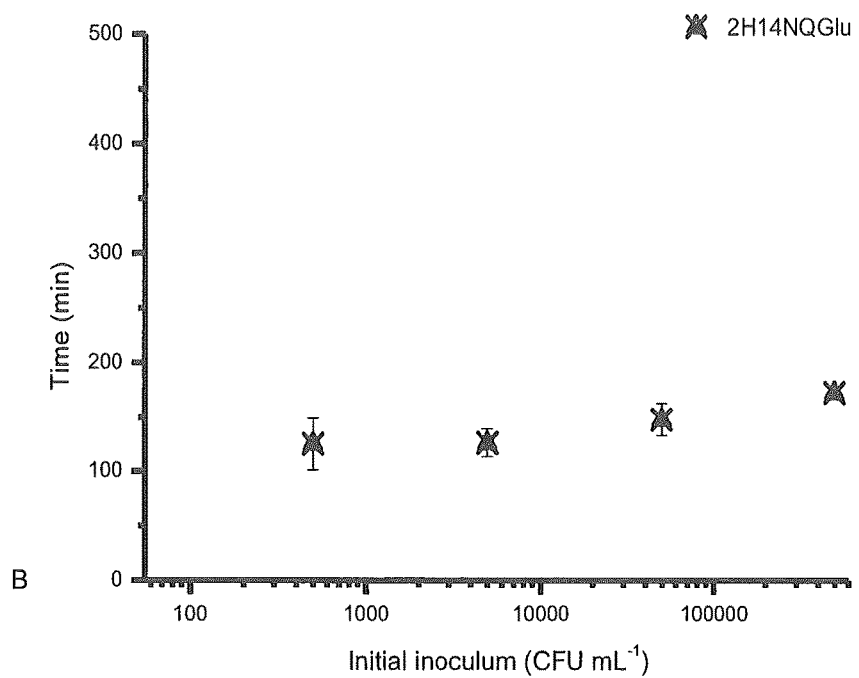
FIG. 6 shows detection time for a mixed inoculum of A. hydrophila and E. coli at 44.5° C. 2H14NQGlu. The initial inoculum of mixed culture represents that of A. hydrophila while the initial E. coli inoculum is kept at $5.0 \times 10^5$ CFU mL-1 (Error bars±1×standard deviation, n=3).

*hydrophila* to the detection signal was minor (FIG. 6). However, there was some attenuation of the detection time when the ratio of *A. hydrophila* to *E. coli* was high (0.1:1 and 1:1, FIG. 6) suggesting a competitive effect between *A. hydrophila* and *E. coli*. While not expected to exhibit glucuronidase activity at this temperature, *A. hydrohila* remained viable, demonstrated by an increase in the electrochemical signal when the temperature of incubation is decreased from 44.5° C. to 37° C. or 30° C., which may explain the attenuation of the signal. Instead of *A. hydrophila* leading to false positive in this electrochemical β-glucuronidase test, where its presence led to the overestimation of *E. coli* in a sample, a slight effect in the opposite direction was documented for 2H14NQGlu detection of *E. coli* β-glucuronidase. In a real situation, this would manifest as a slight underestimation of the total number of *E. coli* in the sample. However, as this effect is only apparent at both high inoculum density and when the relative concentration of *A. hydrophila* compared to *E. coli* is high, it is not expected to pose significant problems in field applications, neither would the extent of interference be above that which would be expected with chromogenic β-glucuronidase enzymatic tests. Interestingly, the reported electrochemical activity of *A. hydrophila* (which would be non-specific and independent of the presence of an electrochemically active aglycon) appears not to be an issue at 44.5° C. The electrochemical activity of *A. hydrophila*, thought to be through direct electron transfer via c-type cytochromes, was shown to be dependent on growth condition. It is noteworthy to mention a temperature dependence (Pham et al., FEMS Microbiol. Lett. 2003; 223:129-134).

It has been demonstrated that the utility of the electrochemical glycoconjugates is likely to be equivalent to their commercially available chromogenic counterparts. Nonetheless, it is clear that the presence of environmental organisms will have an effect on the accuracy of the detection times in field settings. This problem is not constrained to the electrochemical enzymatic tests but would be present in any enzymatic method using glycoconjugates to detect the presence of β-glucuronidase or β-galactosidase. The negative effect of non-target organisms is usually overcome by inclusion of a selective medium in detection systems. The most common component of selective media for Enterobacteriacea is bile salts. Non-target organisms that interfere with enzymatic coliforms or *E. coli* detection assays can be suppressed by several specific inhibitors that can be incorporated into the medium. Examples include antifungals such as amphotericin and rosolic acid to suppress Enterobacteriacea that grow at 44.5° C. (e.g. *Staphylococcus aureus*); and cephalosporins such as cefsulodin that selectively inhibit Aeromonads (Manafi. International Journal of Food Microbiology 2000; 60:205-218; Geissler et al., Journal of Applied Microbiology 2000; 88:280-285; Presswood and Strong. Appl. Environ. Microbiol. 1978; 36:90-94). The ideal medium for electrochemical detection of *E. coli* and coliforms will need to suppress non target fungi and bacteria while being compatible with the chosen biolelectroanalytical method.

Example 10

Detection Limit

Figure 7:
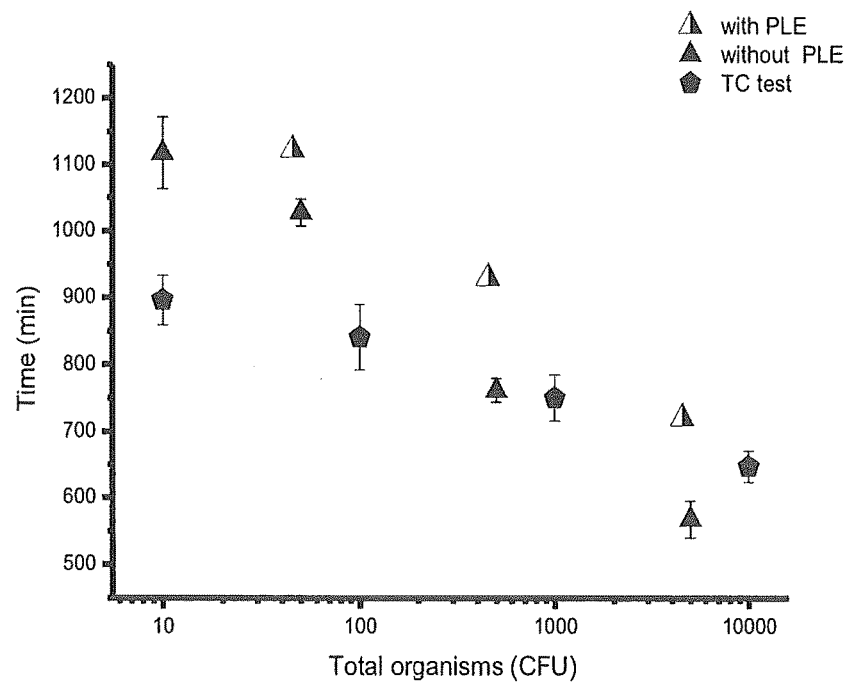
FIG. 7 shows a plot of detection time of E. coli at 44.5° C. with 2H14NQGlu at different normalised initial organism concentrations of 10, 50, 500 and 500 and 5000 CFU mL-1 compared with a commercial detection system of 10, 100, 1000, and 1000 CFU mL-1. (Error bars±1×standard deviation, n=1 except for commercial system, n=5). Detection times with porcine esterase in inoculum sizes of 50, 500 and 500 CFU mL-1 to investigate if different detection times can be achieved from the acid form of the molecule compare with the peracetylated methyl esters (Error bars±1×standard deviation, n=1 except).

While inoculum sizes in the range $5 \times 10^2$-$5 \times 10^5$ CFU $mL^{-1}$ have been used to demonstrate proof of principle, it is acknowledged that this is not the ideal range for commercial detection purposes. Bearing in mind that the setups described here have not been optimized, the inventors decided to extend the detection down to 1 CFU $mL^{-1}$ to further investigate the current limits of this technique for TC detection in ECs and BESs. At 44.5° C., the detection time for CFU $mL^{-1}$ of *E. coli* in an electrochemical system is ~19 h and progresses in a negatively linear fashion to less than 10 h for an inoculum size of 500 CFU $mL^{-1}$. A popular, regulatory approved chromogenic test offers detection of 0.01 CFU $mL^{-1}$ in drinking water in 24 h. However, at low inoculum size, the reproducibility in the detection time decreases (FIG. 7) and is to be expected as differences in inoculum size begin to have a disproportionate contribution to the error of the technique. With the small volume ECs, achieving commercial detection targets (0.01 CFU $mL^{-1}$) is difficult as the average number of cells per reactor would be less than 1 CFU, increasing the probability that the natural variation in inoculum density would lead to 0 CFU in some reactors. To solve this problem would require a larger volume EC and the application of an iterative statistical approach, which is unpractical with the current system. A commercially available and regulatory approved *E. coli* detection system that uses an automated chromogenic method with a similar time-to-detection quantification procedure as used here can quantify 10 organism around 15 h (James et al., PATHOGEN DETECTION SYSTEMS, INC. AUTOMATED MICROBIOLOGY PLATFORM. 2010. EPA) compared to 19 h achieved with our system. However, we achieved similar detection times of 12.5 h for 500 organisms and faster detection times of ~9 h for 5000 organisms compared to 13.5 h for the commercial technique. It is essential to note, however, that the conditions in each test are not comparable so a direct comparison is unwise, nonetheless the data are illustrative that there is huge scope for improving our technique. (James et al., PATHOGEN DETECTION SYSTEMS, INC. AUTOMATED MICROBIOLOGY PLATFORM. 2010. EPA).

Example 11

Figure 8:
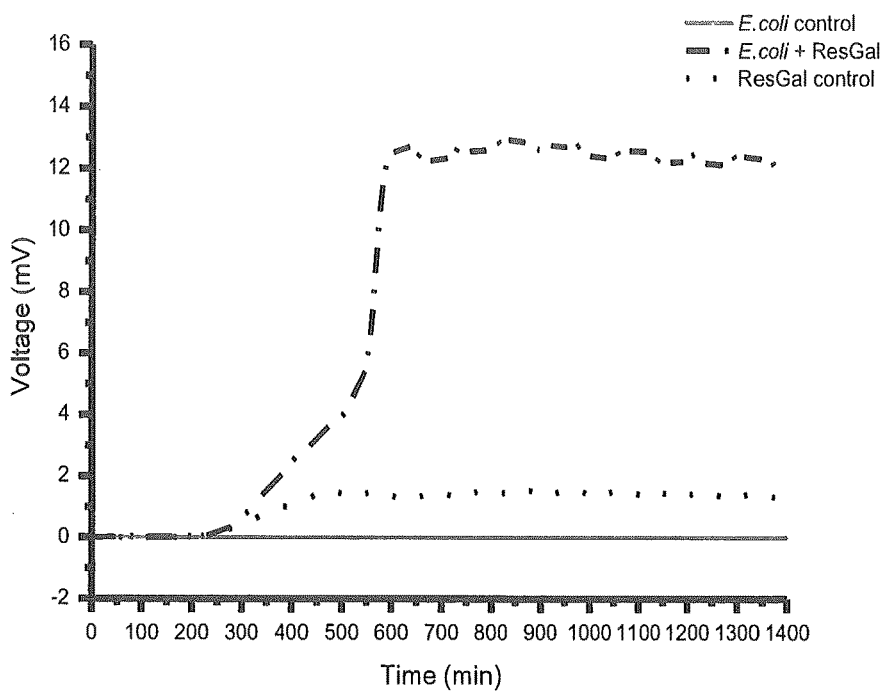
FIG. 8 shows a plot of voltage production in a self-powering bioelectrochemical system inoculated with 500000 CFU $ml^{-1}$ at 30° C. in modified M9 media with ResGal control, positive E.coli control and E.coli supplemented with ResGal.

Electrochemical Detection of *E.coli* using ResGal in a Bioelectrochemical System As shown in FIG. 8, voltage production in a self-powering bioelectrochemical system inoculated with 500000 CFU $ml^{-1}$ at 30° C. in modified M9 media with ResGal control, positive *E.coli* control and *E.coli* supplemented with ResGal was measured.

Example 12

Figure 9:
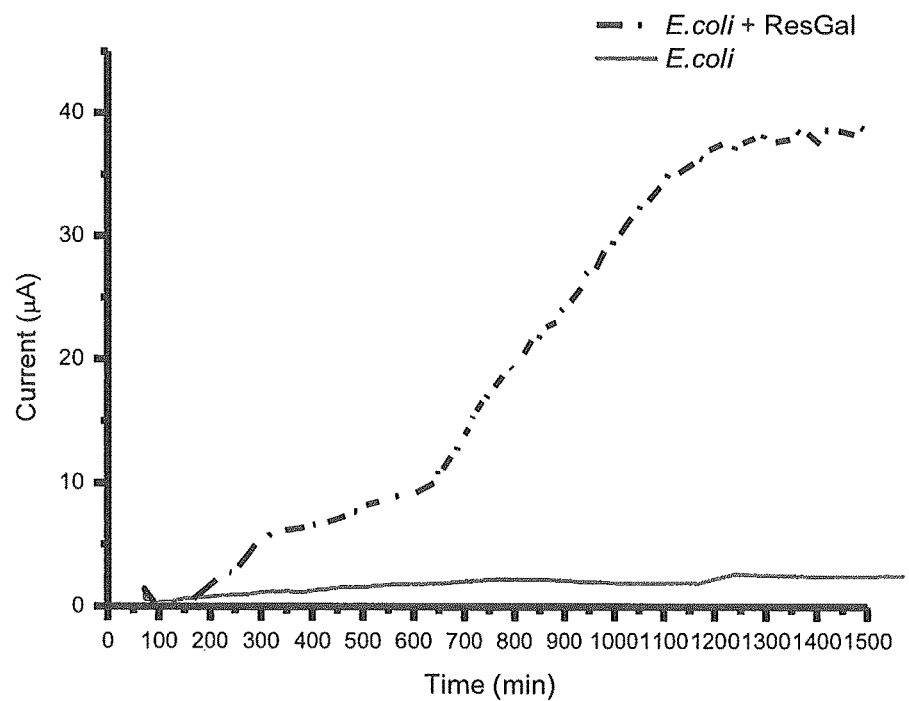
FIG. 9 shows a plot of electrochemical detection of E.coli at initial inoculum of 500000 CFU $ml^{-1}$ with and without ResGal at 30° C. in modified M9 media.

Electrochemical Detection of *E.coli* using ResGal in an Electrochemical System As shown in FIG. 9, electrochemical detection of *E.coli* at initial inoculum of 500000 CFU $ml^{-1}$ with and without ResGal at 30° C. in modified M9 media was carried out in an electrochemical system.

Example 13

Figure 10:
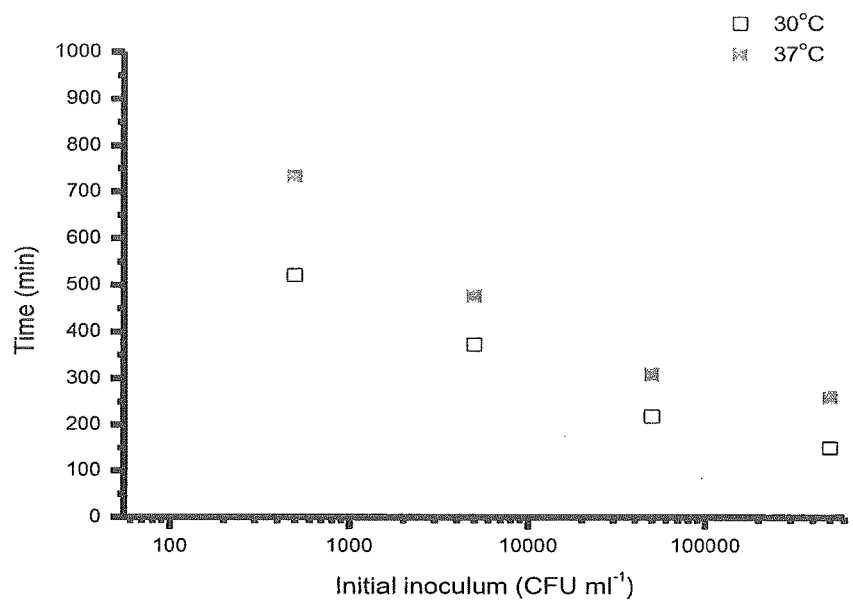
FIG. 10 shows a detection time plot of E.coli in an electrochemical system at initial inoculum of 500, 5000, 50000, 500000 CFU $ml^{-1}$ with ResGal at 30° C. and 37° C. Detection time was taken as time after inoculation of E.coli when the current increase was three times the standard deviation of baseline.

Electrochemical Detection of *E.coli* using ResGal in an Electrochemical System As shown in FIG. 10, electrochemical detection of *E.coli* in an electrochemical system at initial inoculum of 500, 5000, 50000, 500000 CFU $ml^{-1}$ with ResGal at 30° C. and 37° C. was carried out. Detection time was taken as time after inoculation of *E.coli* when the current increase was three times the standard deviation of baseline.

Example 14

Figure 11:
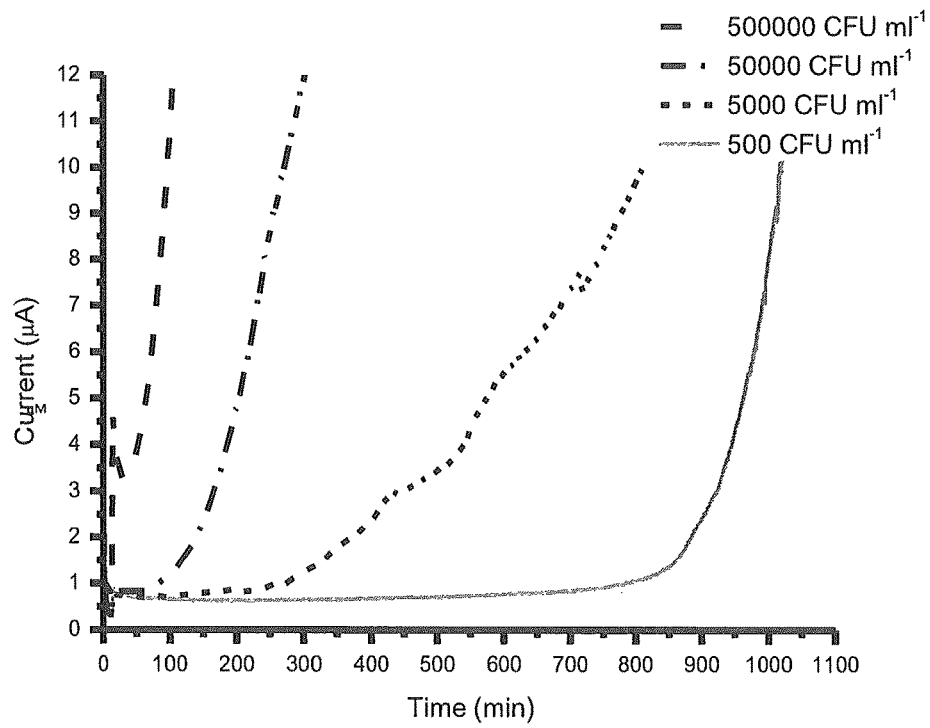
FIG. 11 shows a plot of electrochemical detection of E.coli at initial inoculum of 500, 5000, 50000, 500000 CFU $ml^{-1}$ supplemented with 2H14NQGlu at 37° C. in an electrochemical system. Note the relationship between inoculum size and the onset of the signal. When the signal exceeds 3 times the standard deviation of the baseline, a detection event is recorded and can be used to construct a standard curve

Electrochemical Detection of *E.coli* using 2H14NQGlu in an Electrochemical System As shown in FIG. 11, electrochemical detection of *E.coli* at initial inoculum of 500, 5000, 50000, 500000 CFU ml$^{-1}$ was carried out using 2H14NQGlu at 37° C. in an electrochemical system. Note the relationship between inoculum size and the onset of the signal. When the signal exceeds 3 times the standard deviation of the baseline, a detection event is recorded.

Example 15

Figure 12:
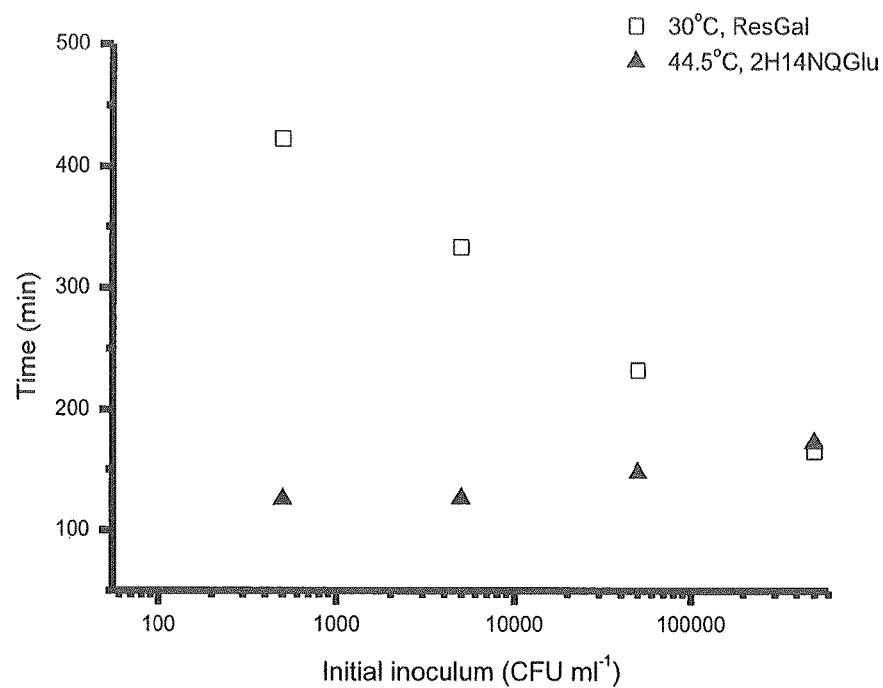
FIG. 12 shows a plot of detection time of mixed culture of Aeromonas hydrophila and E.coli in an electrochemical system. In each mixed culture, E.coli initial inoculum was kept constant at 500000 CFU $ml^{-1}$ while Aeromonas hydrophila was inoculated at initial inoculum of 500, 5000, 50000, 500000 CFU $ml^{-1}$. The mixed culture was observed with ResGal at 30° C. and 2H14NQGlu at 44.5° C. Detection time was taken as time after inoculation of E.coli when the current increase was three times the standard deviation of baseline. The data indicates that A. hydorphpila affects the detection of E. coli when galctopyranosides are used as the sugar moieties and that this can be overcome by increasing the temperature to 44.5° C. and using glucopyranoside reporters and demonstrates selectivity similar to that which would be expected from chromogenic equivalents.

Electrochemical Detection of Mixed Culture of *Aeromonas hydrophila* and *E.coli* using ResGal and 2H14NQGlu in an Electrochemical System As shown in FIG. 12, electrochemical detection of mixed culture of *Aeromonas hydrophila* and *E.coli* was carried out in an electrochemical system. In each mixed culture, *E.coli* initial inoculum was kept constant at 500000 CFU ml$^{-1}$ while *Aeromonas hydrophila* was inoculated at initial inoculum of 500, 5000, 50000, 500000 CFU mr$^{-1}$. The mixed culture was observed with ResGal at 30° C. and 2H14NQGlu at 44.5° C. Detection time was taken as time after inoculation of *E.coli* when the current increase was three times the standard deviation of baseline. The data indicates that *A. hydrophpila* affects the detection of *E. coli* when galctopyraonides are used as the sugar moieties and that this can be overcome by increasing the temperature to 44.5° C. and using glucopyranoside reporters and demonstrates selectivity similar to that which would be expected from chromogenic equivalents.

Example 16

Figure 13:
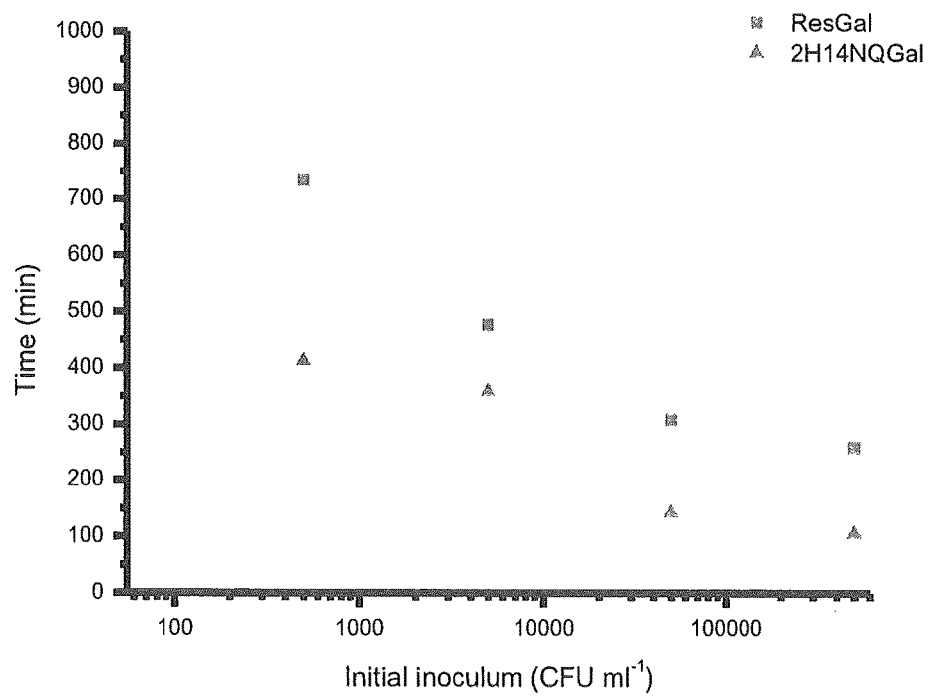
FIG. 13 shows a plot of detection time plot of E.coli in an electrochemical system at initial inoculum of 500, 5000, 50000, 500000 CFU $ml^{-1}$ with 2 galactopyranoside conjugates; ResGal and 2H14NQGal. Detection time was taken as time after inoculation of E.coli when the current increase was three times the standard deviation of baseline. This demonstrates improved detection with naphthoquinone glycoconjugates.

Electrochemical Detection of *E.coli* using ResGal and 2H14NQGal in an Electrochemical System As shown in FIG. 13, electrochemical detection of *E.coli* in an electrochemical system at initial inoculum of 500, 5000, 50000, 500000 CFU ml$^{-1}$ with 2 galactopyranoside conjugates; ResGal and 2H14NQGal. Detection time was taken as time after inoculation of *E.coli* when the current increase was three times the standard deviation of baseline. This demonstrates improved detection with naphthoquinone glycoconjugates.

Example 17

Figure 14:
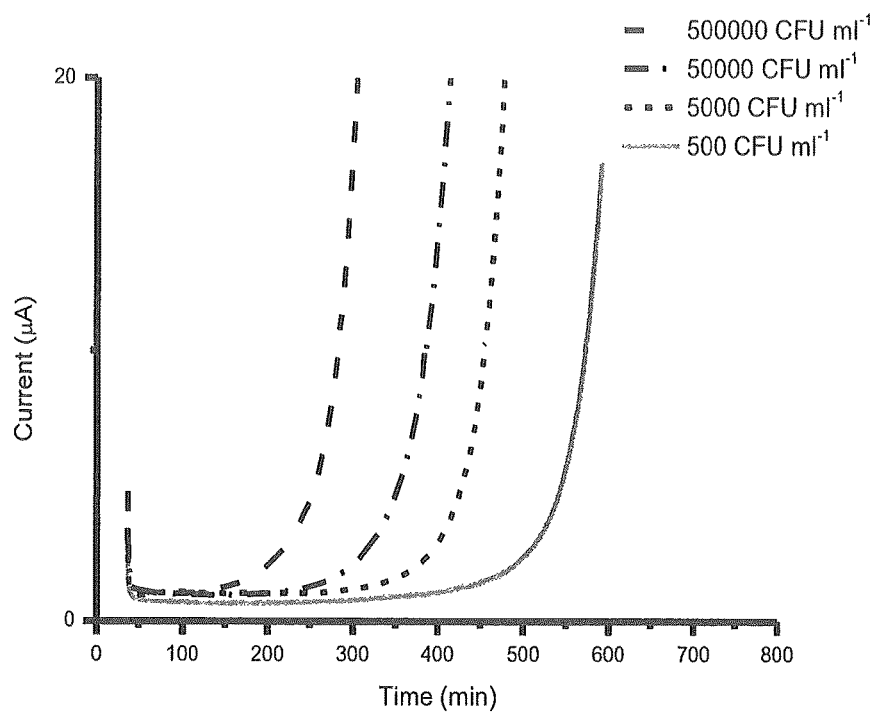
FIG. 14 shows a plot of relatinship between E.faecalis OG1RF inoculum size (500, 5000, 50000, 500000 CFU $ml^{-1}$) supplemented with resorufin β-glucoside (ResGP) at 37° C. This raw data can be used to construct a standard curve for quantification of E. faecalis.
Figure 15:
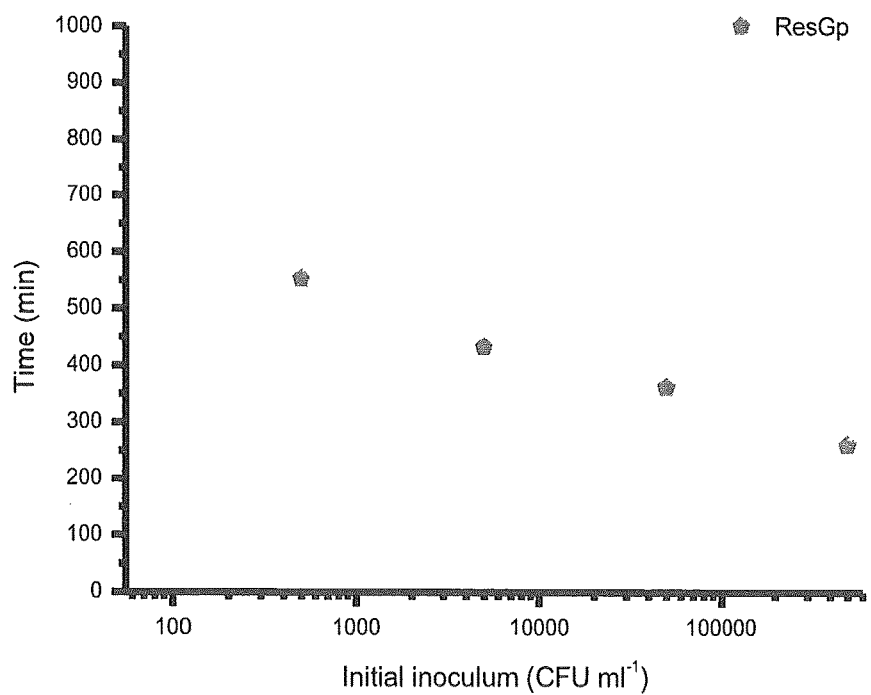
FIG. 15 shows a plot of detection time plot of E.faecaalis OG1RF at initial inoculum of 500, 5000, 50000, 500000 CFU $ml^{-1}$ supplemented with ResGP at 37° C. Detection time was taken as time after inoculation of E.coli when the current increase was three times the standard deviation of baseline.

Electrochemical Detection of *E.faecalis* using ResGlu in an Electrochemical System As shown in FIGS. 14 and 15, electrochemical detection of *E.faecalis* OG1RF was carried out using ResGlu at 37° C. in an electrochemical system. Four initial inoculum sizes (500, 5000, 50000, 500000 CFU ml$^{-1}$) were tested. The raw data can be used to construct a standard curve for quantification of *E. faecalis*. Detection time was taken as time after inoculation of *E. coli* when the current increase was three times the standard deviation of baseline.

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims In addition, where features or aspects of the invention are described in terms of Markush groups, those skilled in the art will recognize that the invention is also thereby described in terms of any individual member or subgroup of members of the Markush group.

What is claimed is:

1. A method for determining the presence of a microorganism in a sample using an electrochemically active reporter, wherein the method comprises
   (a) contacting the sample with an electrochemically active reporter,
   wherein the electrochemically active reporter is a conjugate comprising a sugar moiety and a redox active reporter moiety that are covalently linked such that the covalent bond can be enzymatically cleaved in the presence of the microorganism by an enzyme expressed by the microorganism, wherein the redox active reporter moiety is selected from the group consisting of compounds of formula (I) and resorufin

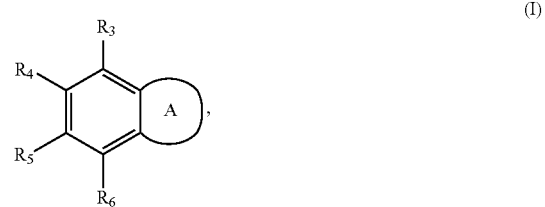

wherein A is an aryl or heteroaryl ring of formula (II) or (III):

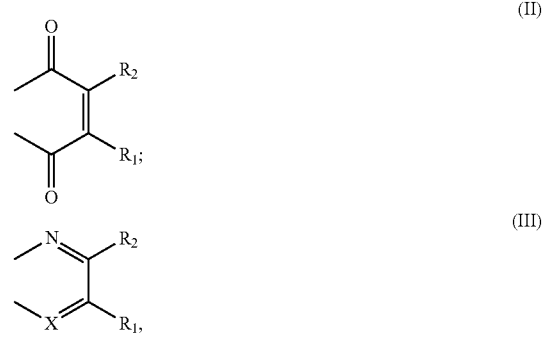

each of $R_1$-$R_6$ is independently selected from the group consisting of H, $NR_7R$, $C_{1-10}$ alkyl, $OR_7$, or $R_1$ and $R_2$ combine to form together with the carbon atoms to which they are attached a 5-6 membered alicyclic or aryl ring, wherein the alicyclic or aryl ring is substituted or unsubstituted, and if substituted the substituents are one or more groups selected from $NR_7R_8$, $C_{1-10}$ alkyl, and $OR_7$;

X is N or $S^+$;

$R_7$ and $R_8$ are independently selected from the group consisting of H, C(O)—$R_9$, $C_{1-10}$ Alkyl;

$R_9$ is $C_{1-10}$ Alkyl;

under conditions that allow enzymatic cleavage of the covalent bond between the sugar moiety and the redox active reporter moiety and reduction of the redox active report moiety in the presence of the microorganism;

(b) electrochemically determining the released redox active reporter moiety; and (c) determining the presence of the microorganism and, optionally, number of the microorganisms in the sample based on the determined released redox active reporter moiety.

2. The method of claim 1, wherein the method is carried out by a 3-electrode electrochemical system or a 2-electrode self-powering bioelectrochemical system comprising a working electrode and an electrolyte.

3. The method of claim 2, wherein step (a) comprises adding the sample and an effective amount of the electrochemically active reporter to the electrolyte.

4. The method of claim 3, wherein step (b) comprises measuring the electrical current or voltage resulting from the released redox active reporter moiety by chronoamperometry, potentiometry or voltammetry or other standard electrochemical techniques using the electrochemical system or by determining the potential difference between the anode and cathode in the self-powering bioelectrochemical system.

5. The method of claim 4, wherein the released redox active reporter is oxidized by interaction with the working electrode, and wherein the oxidized released redox active reporter is reduced by the microorganism and recycled for the generation of electrical current or voltage.

6. The method of claim 1, wherein step (c) comprises determining the number of the microorganisms in the sample based on the electrical current or voltage measured by comparing it to a predetermined standard curve.

7. The method of claim 1, wherein the microorganism is allowed to recover from dormancy or stress prior to being subjected to the detection.

8. The method of claim 1, wherein the microorganism is filtered or concentrated prior to being subjected to the detection.

9. The method of claim 1, wherein an agent is added to the sample to suppress microorganisms other than the target microorganism to be determined.

10. The method of claim 1, wherein the sugar moiety is a pyranose moiety, selected from the group consisting of β-D-glucopyranoside, β-D-galactopyranoside and β-D-glucuronide, and methyl ester, peracetylated and peracetylated methyl ester derivatives thereof.

11. The method of claim 10, wherein the electrochemically active reporter is selected from the group consisting of resorufin-β-D-glucopyranoside, methyl ester resorufin-β-D-glucopyranoside, peracetylated resorufin-β-D-glucopyranoside, peracetylated methyl ester resorufin-β-D-glucopyranoside, resorufin-β-D-galactopyranoside, methyl ester resorufin-β-D-gal actopyranoside, peracetylated resorufin-β-D-galactopyranoside, peracetylated methyl ester resorufin-β-D-galactopyranoside, resorufin-β-D-glucuronide, methyl ester resorufin-β-D-glucuronide, peracetylated resorufin-β-D-glucuronide, peracetylated methyl ester resorufin-β-D-glucuronide, 2-hydroxy-1,4-naphthoquinone-β-D-glucopyranoside, methyl ester 2-hydroxy-1,4-naphthoquinone-β-D-glucopyranoside, peracetylated 2-hydroxy-1,4-naphthoquinone-β-D-glucopyranoside, peracetylated methyl ester 2-hydroxy-1,4-naphthoquinone-β-D-glucopyranoside, 2-hydroxy-1,4-naphthoquinone-β-D-galactopyranoside, methyl ester 2-hydroxy-1,4-naphthoquinone-β-D-galactopyranoside, peracetylated 2hydroxy-1,4-naphthoquinone-β-D-galactopyranoside, peracetylated methyl ester 2-hydroxy-1,4-naphthoquinone-β-D-galactopyranoside, 2-hydroxy-1,4-naphthoquinone-β-D-glucuroni de, methyl ester 2-hydroxy-1,4-naphthoquinone-β-D-glucuronide, methyl ester 2-hydroxy-1,4-naphthoquinone-β-D-glucuronide, peracetylated 2-hydroxy-1,4-naphthoquinone-β-D-glucuronide, peracetylated methyl ester 2-hydroxy-1,4-naphthoquinone-β-D-glucuronide, 5-hydroxy-1,4-naphthoquinone-β-D-glucopyranoside, methyl ester 5-hydroxy-1,4-naphthoquinone-β-D-glucopyranoside, peracetylated 5-hydroxy-1,4-naphthoquinone-β-D-glucopyranoside, peracetylated methyl ester 5-hydroxy-1,4-naphthoquinone-β-D-glucopyranoside, 5-hydroxy-1,4-naphthoquinone-β-D-galactopyranoside, methyl ester 5-hydroxy-1,4-naphthoquinone-β-D-gal actopyranoside, peracetylated 5-hydroxy-1,4-naphthoquinone-β-D-gal actopyranosi de, peracetylated methyl ester 5-hydroxy-1,4-naphthoquinone-β-D-galactopyranoside, 5-hydroxy-1,4-naphthoquinone-β-D-glucuronide, methyl ester 5-hydroxy-1,4-naphthoquinone-β-D-glucuronide, peracetylated 5-hydroxy-1,4-naphthoquinone-β-D-glucuronide, peracetylated methyl ester 5-hydroxy-1,4-naphthoquinone-β-D-glucuronide, 5,8-dihydroxy-1,4-naphthoquinone-β-D-glucopyranoside, methyl ester 5,8-dihydroxy-1,4-naphthoquinone-β-D-glucopyranoside, peracetylated 5,8-dihydroxy-1,4-naphthoquinone-β-D-glucopyranosi de, peracetylated methyl ester 5,8-dihydroxy-1,4-naphthoquinone-β-D-glucopyranoside, 5,8-dihydroxy-1,4-naphthoquinone-β-D-galactopyranoside, methyl ester-5,8-dihydroxy-1,4-naphthoquinone-β-D-galactopyranoside, peracetylated 5,8-di hydroxy -1,4-naphthoquinone-β-D-galactopyranoside, peracetylated methyl ester-5, 8-di hy droxy-1,4-naphthoquinone-β-D-galactopyranoside, 5,8-dihydroxy-1,4-naphthoquinone-β-D -glucuronide, methyl ester-5,8-dihydroxy-1,4-naphthoquinone-β-D-glucuronide, peracetylated 5,8-dihydroxy-1,4-naphthoquinone-β-D-glucuronide, and peracetylated methyl ester-5,8-dihydroxy-1,4-naphthoquinone-β-D-glucuronide.

12. The method of claim 1, wherein the covalent bond between the sugar moiety and the redox active reporter moiety is cleaved by an enzyme expressed by the microorganism to be determined.

13. The method of claim 12, wherein the expression of the enzyme is induced.

14. The method of claim 1, wherein the method further comprises a step of lysing the cell membrane or enhancing membrane permeability of the microorganism to facilitate the release of the redox active reporter moiety or the enzyme cleaving the electrochemically active reporter.

15. The method of claim 1, wherein the method is a multiplex method that allows simultaneous determination of a number of different organisms.

16. The method of claim 15, wherein for each microorganism to be detected a different electrochemically active reporter is used.

17. The method of claim 1, wherein the microorganism is a coliform bacterium.

18. The method of claim 17, wherein the microorganism is *Escherichia coli*, the enzyme expressed by the microorganism is β-glucuronidase, and the sugar moiety is β-D- glucuronide or a methyl ester, peracetylated or peracetylated methyl ester derivative thereof.

19. The method of claim 17, wherein the microorganism is *Escherichia coli*, the enzyme expressed by the microorganism is β-D-galactosidase, and the sugar moiety is β-D-galactopyranoside or a methyl ester, peracetylated or peracetylated methyl ester derivative thereof.

20. The method of claim 17, wherein the microorganism is *Escherichia coli* or *Enterococcus faecalis*, the enzyme expressed by the microorganism is β-glucosidase, and the sugar moiety is β-D-glucopyranoside or a methyl ester, peracetylated or peracetylated methyl ester derivative thereof.

* * * * *

UNITED STATES PATENT AND TRADEMARK OFFICE
CERTIFICATE OF CORRECTION

PATENT NO. : 10,179,927 B2
APPLICATION NO. : 15/505847
DATED : January 15, 2019
INVENTOR(S) : Jamie Hinks Page 1 of 1

It is certified that error appears in the above-identified patent and that said Letters Patent is hereby corrected as shown below:

In the Claims

Column 29, Line 62 Claim 11:
"resorufin-B-D-gal actopyranoside," should read, --resorufin-B-D-galactopyranoside--

Column 30, Line 23 Claim 11:
"5-hydroxy-1,4-naphthoquinone-B-D-gal actopyranoside," should read, --5-hydroxy-1,4-naphthoquinone-B-D-galactopyranoside,--

Column 30, Line 24-25 Claim 11:
"gal actopyranosi de," should read, --galactopyranoside,--

Column 30, Line 34 Claim 11:
"glucopyranosi de" should read, --glucopyranoside--

Column 30, Line 40 Claim 11:
"8-di hy droxy-1,4-naphthoquinone-" should read, --8-dihydroxy-1,4-naphthoquinone--

Signed and Sealed this
Thirtieth Day of April, 2019

Andrei Iancu
*Director of the United States Patent and Trademark Office*